United States Patent
Shuman et al.

(10) Patent No.: US 6,882,279 B2
(45) Date of Patent: *Apr. 19, 2005

(54) SENSOR OUTPUT ANALOG PROCESSING-A MICROCONTROLLER-BASED INSECT MONITORING SYSTEM

(75) Inventors: Dennis Shuman, Gainesville, FL (US); R. David Crompton, Calgary (CA)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 327 days.

This patent is subject to a terminal disclaimer.

(21) Appl. No.: 10/135,503

(22) Filed: May 1, 2002

(65) Prior Publication Data

US 2002/0185605 A1 Dec. 12, 2002

Related U.S. Application Data

(63) Continuation-in-part of application No. 09/846,277, filed on May 2, 2001, now Pat. No. 6,707,384.

(51) Int. Cl.$^7$ .............................................. G08B 23/00
(52) U.S. Cl. ................................ 340/573.2; 340/573.1; 340/540; 340/566; 250/338.1; 250/336.1; 250/341.1; 250/359.1
(58) Field of Search .......................... 340/573.1, 573.2, 340/540, 566; 250/338.1, 336.1, 343, 358.1, 341.1, 359.1, 574, 222.1; 356/326, 305

(56) References Cited

U.S. PATENT DOCUMENTS

| | | | |
|---|---|---|---|
| 4,410,967 A | 10/1983 | Hendricks | 367/87 |
| 5,005,416 A | 4/1991 | Vick et al. | 73/587 |
| 5,592,774 A * | 1/1997 | Galyon | 43/124 |
| 5,646,404 A * | 7/1997 | Litzkow et al. | 250/338.1 |
| 6,150,944 A * | 11/2000 | Martin et al. | 340/632 |

OTHER PUBLICATIONS

Shuman, D., et al., "An Electronic Fall–Through Probe Insect Counter Computer System for Monitoring Infestation in Stored Product Facilities", *ASAE Meeting Presentation Paper No. 946501*, Atlanta, Georgia, pp. 1–12, Dec. 13–16, 1994.

Hook, B., et al., "Digital I/O with the PC", *Dr. Dobbs Journal*, pp. 64–70, Apr. 1994.

White, N.D.G., et al., "The Development and Use of Pitfall and Probe Traps for Capturing Insects in Stored Grain", *Journal of the Kansas Entomological Society*, vol. 63(4), pp. 506–525, Jul. 15, 1990.

Reed, C.R., et al., "Pitfall Traps and Grain Samples as Indicators of Insects in Farm–Stored Wheat", *Journal Econ. Entomol.*, vol. 84(4), pp. 1381–1387, Aug. 1991.

Hagstrum et al., *Proceedings 6th International Working Conference on Stored–Product Protection*, Canberra, Australia, 1994, in press.

(Continued)

*Primary Examiner*—Hung Nguyen
(74) *Attorney, Agent, or Firm*—John D. Fado; Gail E. Poulos

(57) ABSTRACT

A system for automated monitoring of pest insects in stored products to help identify insect species and improve reliability across adverse external conditions, including environmental, biological and aging. The system includes sensor units having a microcontroller which collects, analyzes, and stores data from at least one signal pulse created by an insect falling through the sensor unit.

26 Claims, 24 Drawing Sheets

Microfiche Appendix Included
(1 Microfiche, 56 Pages)

OTHER PUBLICATIONS

Bauwin, G.R., et al., "Sampling, Inspection, and Grading of Grain", In: *Storage of Cereal Grains and Their Products; 2nd Ed., ed. C.M. Christensen*, pp. 115–157, 1974; St. Paul, MN: American Association of Cereal Chemists.

Noyes, R., et al., "Stored Grain Management Techniques", In: *Management of Grain, Bulk Commodities, and Bagged Products*, Circular E–912, 71–79, Cooperative Extension Service, Oklahoma State University, 1991.

Hagstrum, D., et al., "How to Sample Grain for Insects", In: *Management of Grain, Bulk Commodities, and Bagged Products*, Circular E–912, 65–69, Cooperative Extension Service, Oklahoma State University, 1991.

Hendricks, D.E., "Portable Electronic Detector System Used with Inverted–Cone Sex Pheromone Traps to Determine Periodicity and Moth Captures", *Environmental Entomology*, vol. 14(3), pp. 199–204, Jun. 1985.

Hendricks,, D. E., "Development of an Electronic System for Detecting *Heliothis* spp. Moths (Lepidoptera: Noctuidae) and Transferring Incident Information from the Field to a Computer", *J. Econ. Entomol.*, vol. 82(2), pp. 675–684, Apr. 1989.

Shuman, D., "Infrared Bug–Counter Goes to Disney World", *Greenhouse Product News*, pp. 23–24, Jan. 1995.

Shuman, D., "Infrared Bug–Counter Goes to Disney World", *Agricultural Research Magazine*, p. 31, Oct. 1994.

Petitt, F.L., et al., "An Automated System for Counting and Packaging A Leafminer Parasitoid", *Florida Entomol. Soc.*, Aug. 1994. Poster presentation and press release by Sean Adams.

Subramanyam, BH., et al., "Accuracies and Sample Sizes Associated with Estimating Densities of Adult Beetles (Coleoptera) Caught in Probe Traps in Stored Barley", *J. Econ. Entomol.*, vol. 83(3), pp. 1102–1109 , Jun. 1990.

Subramanyam, BH., et al., "Insects Infesting Barley Stored on Farms in Minnesota", *J. Econ. Entomol.* , vol. 82(6), pp. 1817–1824, Dec. 1989.

Barak, A.V., et al., "Factors Affecting the Design of Traps for Stored–Product Insects", *Journal of the Kansas Entomological Society*, vol. 63(4), pp. 466–485, 1990.

Cuperus, G.W., et al., "Variables Affecting Capture of Stored–Grain Insects in Probe Traps", *Journal of the Kansas Entomological Society*, vol. 63(4), pp. 486–489, 1990.

Wei, Y., et al., "Computerized Remote Control System for Monitoring Dynamics of Insect Population in Bulk Stored Grain", *6th International Working Conference on Stored Product Protection*, Canberra, Australia, Apr. 1994.

Shuman, D., et al., "Automated Monitoring of Stored–Grain Insects: Acoustical and Electronic Probe Methods", Presentation: *Annual International Research Conference on Methyl Bromide Alternatives and Emissions Reductions* , Nov. 1994.

Shuman, D., "Electronic Detection of Insects in Grains", Hand–out at ARS/FGIS Working, with Non–Gov't People Present, Oct. 25, 1991.

Subramanyam, BH., et al., "Field Tests with Probe Traps for Sampling Adult Insects Infesting Farm–Stored Grain", *J. Agric. Entomol.* , vol. 6(1), pp. 9–21, Jan. 1989.

Trece Incorporated, *Storgard WB Probe II Insect Monitoring System*, 1 page.

AgriSense BCS Ltd., Trappit Insect Probe Trap (Technical Information), 1 page.

Automata, Inc., Remote Counting of Insects with "Bug Counter" and Data Lynx Telemetry Equipment (Technical Information), 2 pages.

\* cited by examiner

SENSOR OUTPUT ANALOG PROCESSING-A MICROCONTROLLER-BASED INSECT MONITORING SYSTEM This is a continuation-in-part of application Ser. No. 09/846,277, filed May 2, 2001, now U.S. Pat. No. 6,707,384 which is herein incorporated by reference in its entirety.

MICROFICHE APPENDIX

A Microfiche Appendix containing 1 microfiche containing 56 frames is included.

BACKGROUND OF THE INVENTION

1. Field of the Invention

This invention generally relates to an apparatus and a process for monitoring and/or providing a quantitative and/or qualitative indication of insect infestations in stored products.

2. Description of the Related Art

Protection of stored agricultural commodities from insect infestations and the direct loss caused by insects are costly. Insect infestations in stored agricultural commodities result in annual losses of millions of dollars. Early detection of infestation problems is necessary to initiate timely control measures and eliminate unnecessary "scheduled" insect treatments. Routine use of insecticides to protect stored products may have constraints.

The standard practice for detecting and quantifying infestation in stored grain is visual inspection of samples for adult insects. Insects are usually separated from grain samples with hand or inclined sieves. A traditional method of obtaining samples uses a long, hollow multi-compartment grain trier inserted into the commodity. Its gates are then opened and closed to acquire samples at different depths and, after withdrawal, the samples are removed for inspection (Bauwin et al., In: Storage of Cereal Grains and Their Products; $2^{nd}$ edition, ED: C. M. Christensen, 115–157, 1974; St. Paul, Minn.:American Association of Cereal Chemists). Other methods can get beyond the limitation of only sampling close to the grain's surface. A vacuum probe can extract larger samples from deeper with a grain mass and a grain mass can be turned enabling a pelican sampler to catch samples from the moving grain stream (Noyes et al., In: Management of Grain, Bulk Commodities, and Bagged Products, Circular E-912, 71–79, Cooperative Extension Service, Oklahoma State University, 1991). None of these sampling techniques provide continuous and thorough monitoring. Low insect populations are difficult to detect in small samples and a much greater proportion of the grain needs to be sampled to accurately estimate insect population size (Hagstrum et al., IN: Management of Grain, Bulk Commodities, and Bagged Products, Circular E-912, 65–69, Cooperative Extension Service, Oklahoma State University, 1991). Additionally, theses sampling methods are expensive and labor intensive and therefore not repeated very often even though an infestation can grow from undetectable to damaging levels in two weeks. Another method, employed in some large grain elevators, is temperature sensing cables distributed throughout the storage volume. This system is only sensitive to very high insect populations. Furthermore, both moisture and mold growth can elevate temperature levels.

White et al., (Journal of the Kansas Entomological Society, Volume 63(4), 506–525, 1990) and Reed et al. (Journal of Economic Entomology, Volume 84(4), 1381–1387, 1991) both disclose passive grain probe traps that have been developed. The probes are vertical perforated tubes that insects crawl into and then drop through to be trapped in a reservoir at the lower end. Probes are left in the grain for prolonged periods, allowing them to continuously capture insects and thus detect very low insect populations. However, the information is only available after the labor intensive process of inserting the trap into the grain, waiting, withdrawing the trap, and then inspecting the trap contents. The difficulty of insertion and withdrawal increases with the distance from the surface due to the resistance of the grain.

U.S. Pat. No. 5,005,416 discloses an automated, continuous monitoring electronic grain probe trap with a bottom reservoir fitted with a detector that senses the movements of trapped insects. The number of insects caught in the trap is estimated based on the amount of vibration detected. However, temperature, species, time in the trap, the amount of food, and other insects in the trap are all factors which can affect the trapped insects' vibration producing activity. Vibration detection may also be prone to error from ambient noise.

Hagstrum et al. (Proceedings $6^{th}$ International Working Conference on Stored-Product Protection, Canberra, Australia, Volume 1, 403–405, 1994) disclose a computer-based acoustic system that provides for automated monitoring by detecting insect generated sounds. Piezoelectric transducers, mounted on vertical cables installed in grain bins, sense the feeding and movement sounds of nearby insects. The acoustic sensor outputs are sequentially connected to electronic components that count and relay to a computer, the number of signal peaks crossing a threshold level during each sensor's observation interval.

U.S. Pat. No. 5,646,404 (herein incorporated by reference) discloses an electronic grain probe insect counter (EGPIC) which provides real-time monitoring of insects using infrared beam technology to detect insects as they fall through modified grain probe traps. When an insect falls through the trap, it partially masks an infrared beam. Whenever one of the traps infrared-beam sensor output signals exceeds a precise detector threshold level (this level being set to specify the minimum detectable insect size), the resulting quantitative insect detection or count is recorded and time-stamped to provide an ongoing indication of infestation levels in stored-products. The real-time data acquired by an EGPIC system are used to display the numbers of insects that have been counted within specific commodity regions and time periods. If the rate of insect counts are below a known threshold (based on factors such as economics, tolerance, environmental parameters, etc.), no control action is necessary. However, if the rate is above that threshold, the appropriate response may be a function of the species being counted. This is because the relationship between insect counts and population density is a function of species. Therefore, the appropriate first response may be to go into the commodity storage and identify the species at those probe sites that are getting the high insect counts. Then, with that species information, a decision can be made as to if and what control response is warranted. Thus, while the EGPIC system can eliminate the need to visually inspect the commodity on an ongoing scheduled basis, increasing insect counts may still mandate a visual inspection before control decisions are made. The EGPIC system employs a sensitivity control in order that it not count objects smaller than the smallest stored-product insect of concern (e.g., grain particles). Because of this, smaller insects such as psocids and mites are not counted even though their presence may be of interest to the facility manager. This sensitivity control must be set conservatively (higher sensitivity) in order to ensure that each probe maintains a reasonable count accuracy with the smallest stored-product insect of concern because of large electronic and mechanical component variability across probes. However, this may occasionally lead to false positives due to other very small insects (e.g., psocids) and grain particles. Other potential sources of false positives are electrical impulse noise (e.g., generated by electric machinery) and a crawling or clinging insect managing to get near the infrared beam which can cause a multitude of false counts. The EGPIC system has a self-test feature to insure that receiving no counts from a probe is not an indication of a probe or system failure. At regular time intervals, the system momentarily decreases the infrared beam source output, simulating an insect falling through and masking part of the beam, and then checks whether this "count" is detected. However, this is a pass/fail test, so there is no warning of a gradual performance degradation until failure occurs.

While various methods and systems have been developed for monitoring insect infestations in stored-products, there remains a need in the art for a system for remote monitoring of pest infestations which provides a more accurate count and species identification. The present invention provides a remote system for automatically counting insects which enables a qualitative analysis of an analog sensor output signal to provide additional information that can help identify species, reject erroneous counts, etc. which is different from prior art methods and systems.

SUMMARY OF THE INVENTION

It is therefore an object of the present invention to provide a monitoring system for insect infestations in stored-products that gives both accurate counts and/or qualitative information such as insect species identification.

Another object of the present invention is to provide a monitoring system that counts all objects falling past at least one sensing transducer including those that are not identified as insect species of concern and has the ability to discriminate between the different falling object categories.

A further object of the present invention is to provide a monitoring system that includes at least one sensing transducer for detecting insects falling past said transducer and for statistically identifying insect species.

A still further object of the present invention is to provide a monitoring system that includes at least two beams for detecting insects falling past said transducer and for statistically identifying insect species.

A further object of the present invention is to provide a monitoring system that has a means for obtaining identical response sensitivity from all probes despite large electronic and mechanical component variability across probes.

A still further object of the present invention is to provide a monitoring system which obtains consistent response sensitivity from each probe despite changes resulting from component aging, environmental changes, and potential foreign matter accumulation (e.g., dust, moisture, etc.) on the system's sensing transducer components.

Another object of the present invention is to provide a monitoring system which monitors the ongoing performance of each deployed probe while in situ, thus obtaining an indication of a forthcoming need for probe maintenance before probe failure.

A still further object of the present invention is to provide a monitoring system which improves system accuracy by only counting insects falling past at least one sensing transducer while rejecting potential detection of insects inadvertently loitering in the vicinity of the sensing transducer.

Another object of the present invention is to provide a monitoring system which improves system accuracy by rejecting false detections due to electrical transients (noise spikes).

Further objects and advantages of the invention will become apparent from the following description.

DETAILED DESCRIPTION OF THE INVENTION

Figure 1:
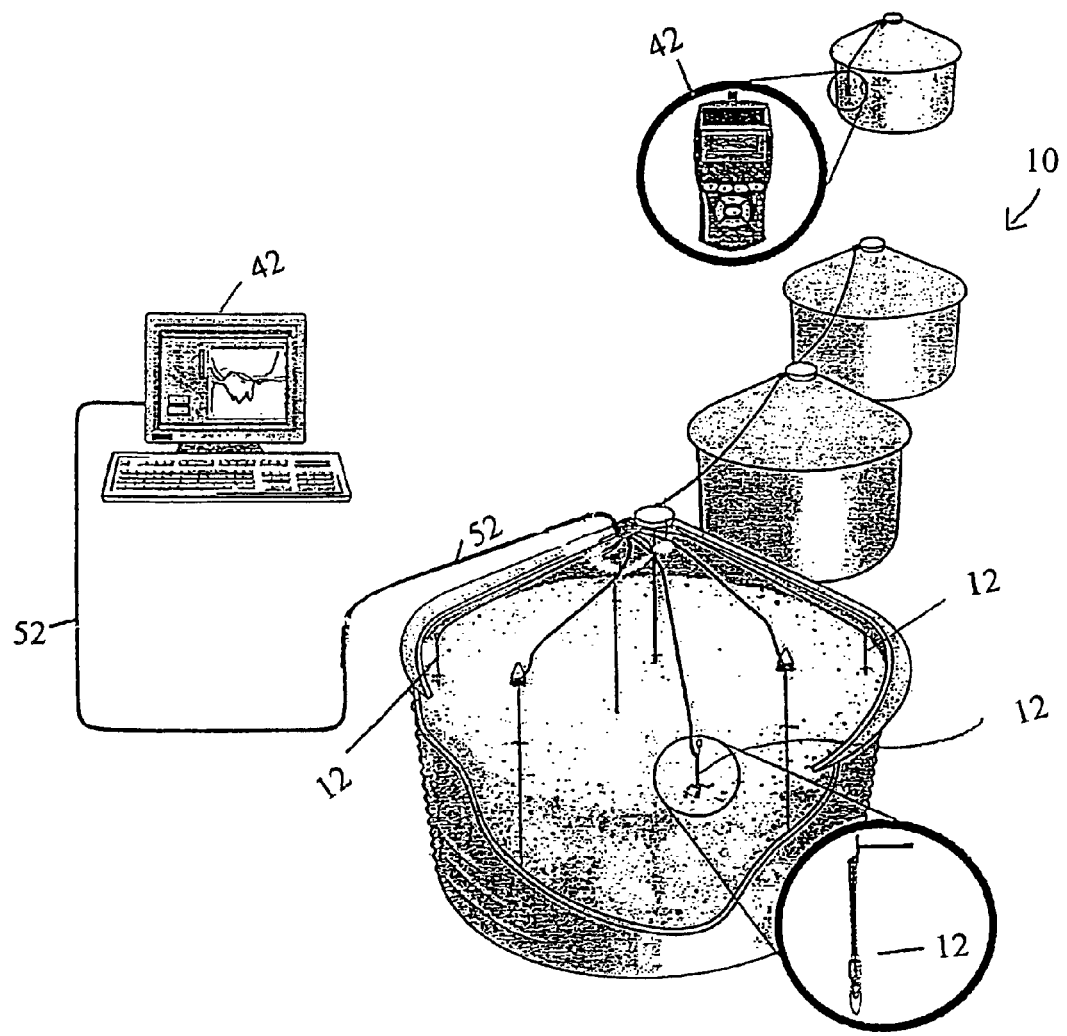
FIG. 1 is a drawing showing placement pattern of a microcontroller-based insect monitoring system in a grain storage facility.
Figure 2:
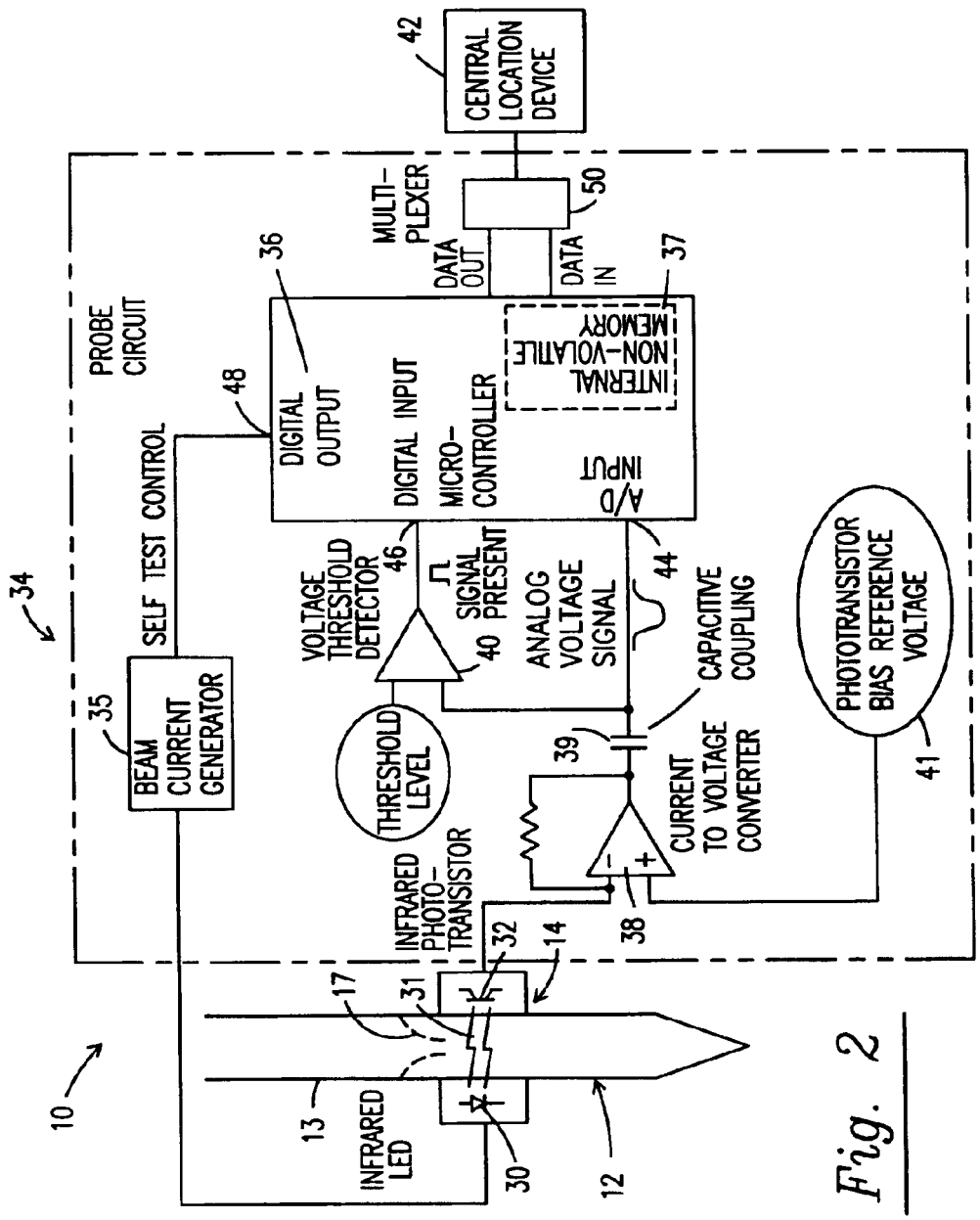
FIG. 2 is a block diagram showing a microcontroller-based insect monitoring system implemented with infrared transducers producing a single beam.
Figure 12:
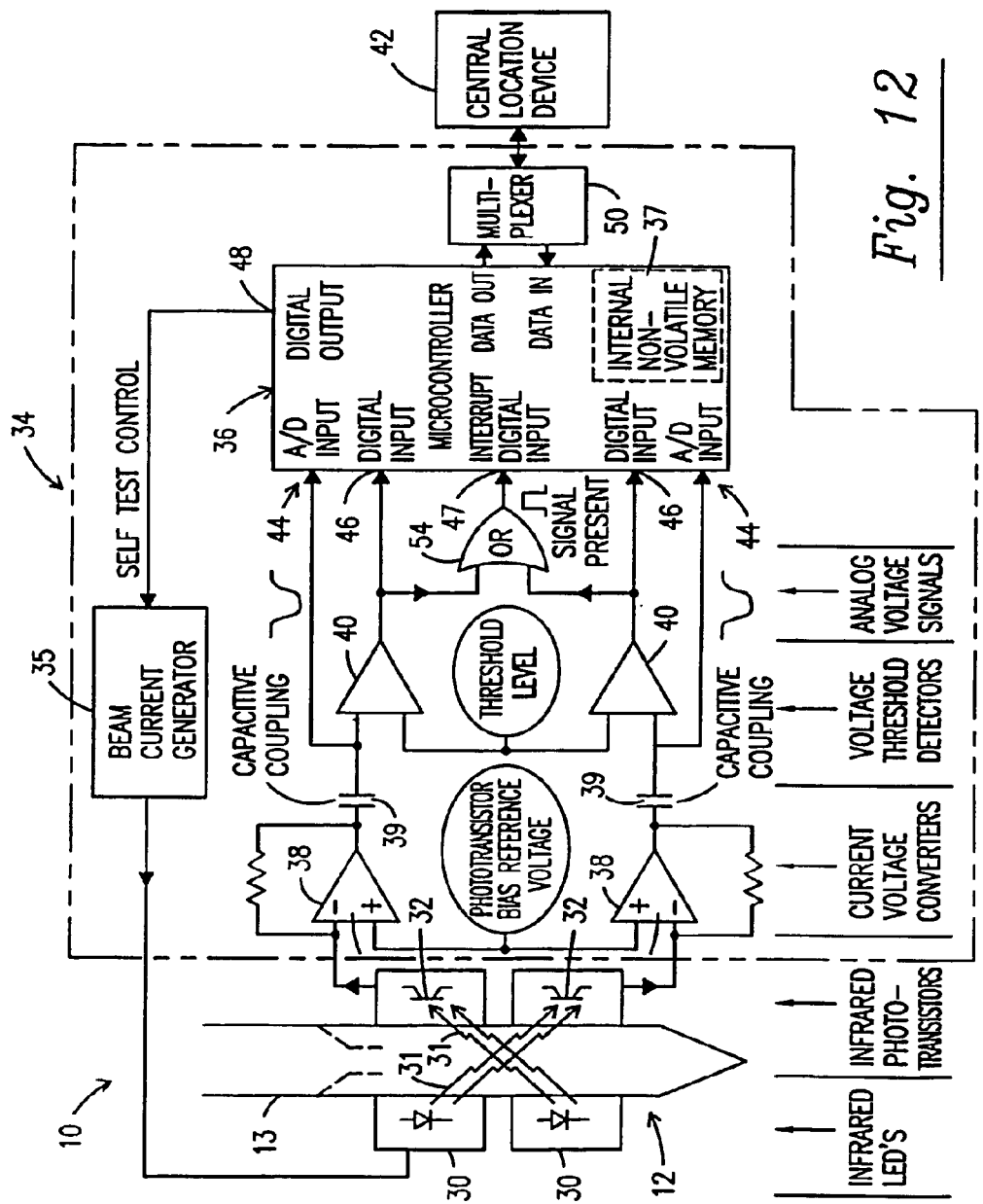
FIG. 12 is a block diagram showing the functional components of a two beam, microcontroller based insect monitoring system.

The present invention is useful for providing a quantitative and/or qualitative detection of insect infestations in stored products such as grains, fruits, nuts, vegetables, and legumes, for example (FIGS. 1, 2, and 12). Enhancement of a grain probe trap with a microcontroller-based insect monitoring system 10, eliminates (a) the labor intensive process involved in its use, (b) the limitations on where it can be located in a storage structure, and (c) the lack of information available from it until removed for the stored commodity and inspected.

Figure 4:
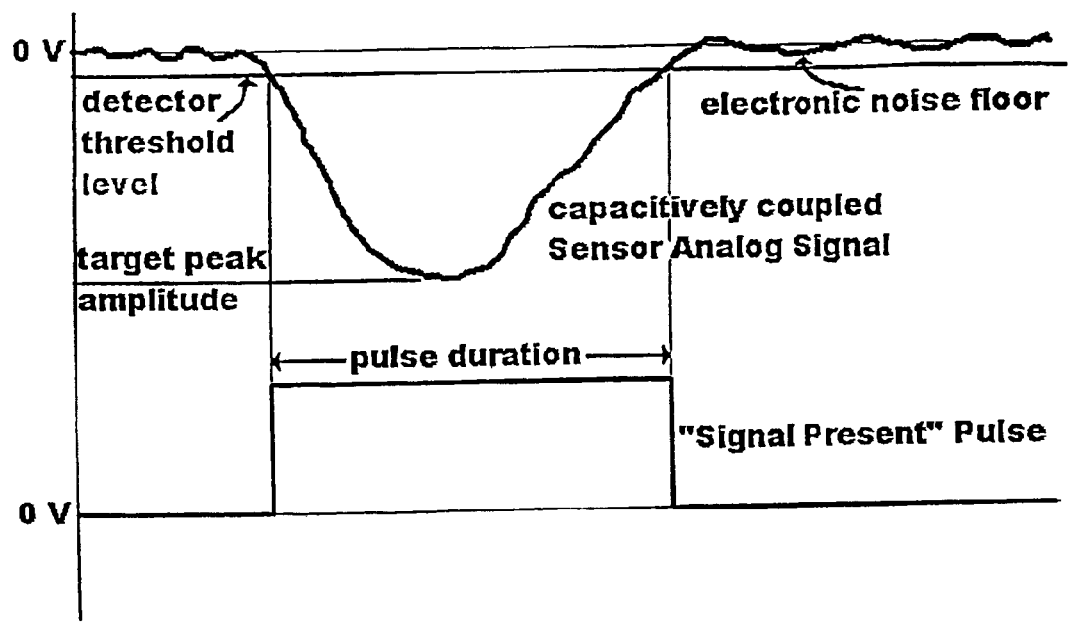
FIG. 4 is a graph showing the waveforms from the sensor output analog processing implementation.

System 10 not only determines when an analog output signal of a sensing transducer 14 exceeds a certain threshold value to generate a digital pulse (FIG. 4) which is then counted; it also acquires and analyzes the sensor 20 output signal waveform to extract additional information from it which is then utilized to determine, for example, (a) what insect species of concern are present, (b) if other objects are entering the probe, (c) the probe's present sensitivity, (d) the need for forthcoming maintenance, and (e) the recognition and subsequent rejection of false positives due to either crawling insects or electrical noise spikes. System 10 can use the generated data to perform additional analyses such as spatial analysis to generate three dimensional insect population contours and to make insect management decisions using predictive models, etc.

System 10 includes at least one sensing transducer 14 with at least one analog output signal which can be, for example, an infrared beam receiver 32 (e.g., a phototransistor), a moisture sensor (e.g., a parallel plate capacitor), etc., and the information extracted from the output waveform of the transducer 14 is primarily its amplitude, its duration, and its time of occurrence. It can also include a smart sensor with built-in analog to digital conversion and signal processing, in which case the invention could be implemented, in whole or in part, in the sensor 20 body itself.

For purposes of illustration, the following detailed description exemplifies the implementation of the present invention using an electronic grain probe insect detector having at least one infrared beam transducer 14 in the sensor head 24, such as for example, as described in U.S. Pat. No. 5,646,404 (Litzkow et al, Jul. 8, 1997; herein incorporated by reference); and Shuman et al. (A Computer-Based Insect Monitoring System for Stored-Products Using Infrared Sensors, presented at Third International Symposium on Sensors; Aug. 17–21, 1997 in Tiberias, Israel; published in Acta Horticulturae, Volume 562, 243–255, 2001 herein incorporated by reference). One of ordinary skill in the art could readily incorporate any type of sensor 20 capable of an analog output in which the waveform peak amplitude is indicative of insect species, given the detailed description provided below.

Figure 3:
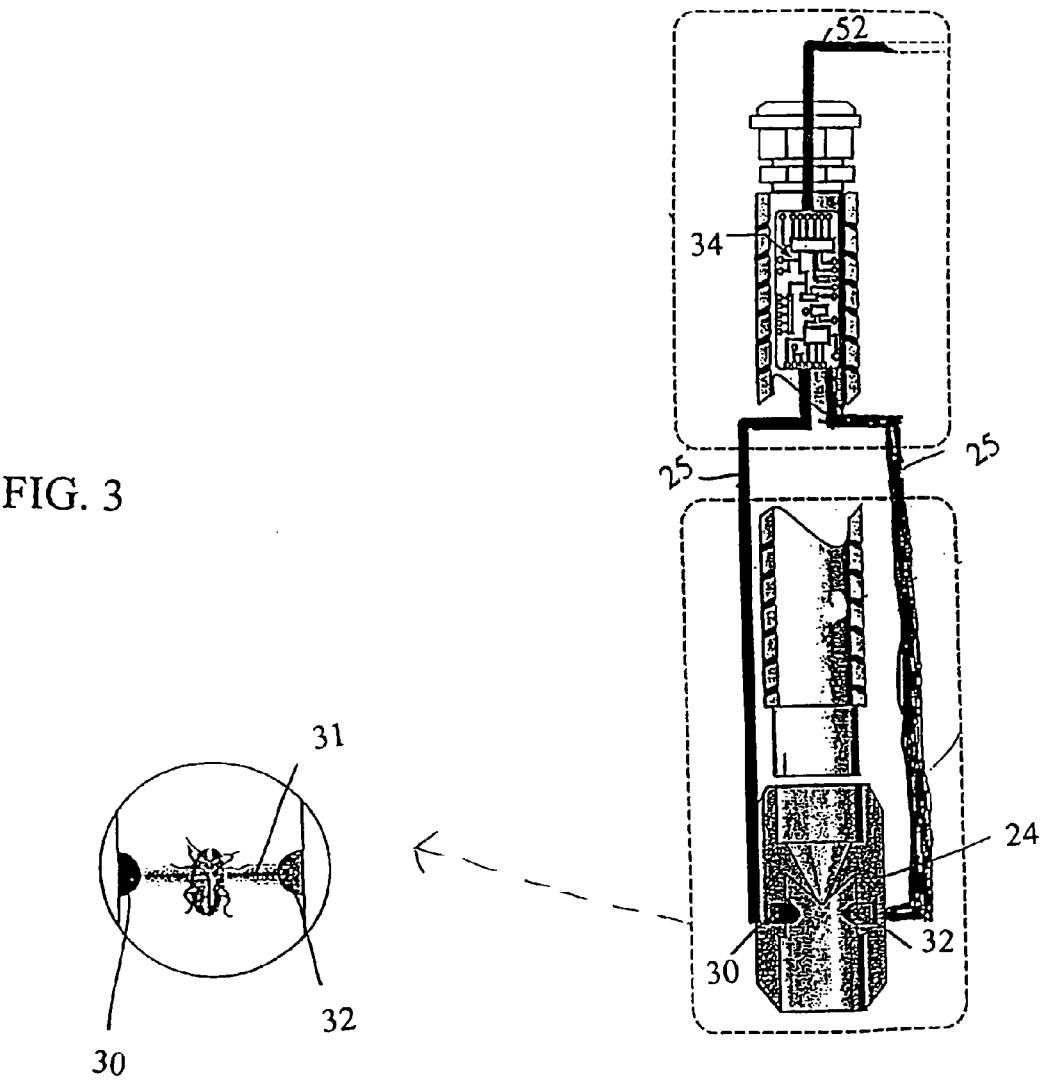
FIG. 3 is a drawing showing the location of temperature sensor 33, probe circuit board 34, and sensor head 24.
Figure 9:
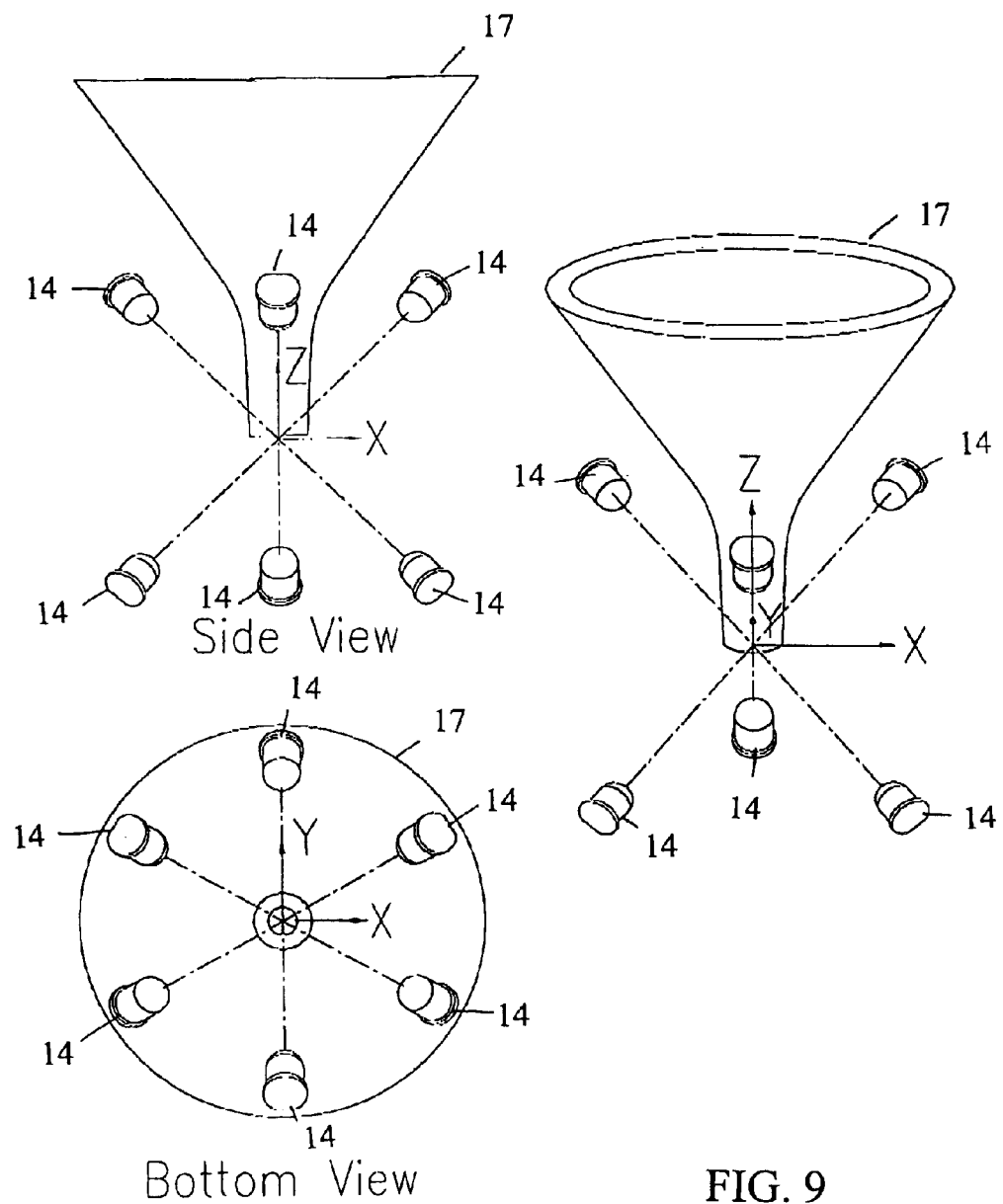
FIG. 9 is a drawing showing how three orthogonal infrared beams can be oriented to intersect underneath the bottom opening of a funnel used to direct the path of a falling insect.
Figure 10:
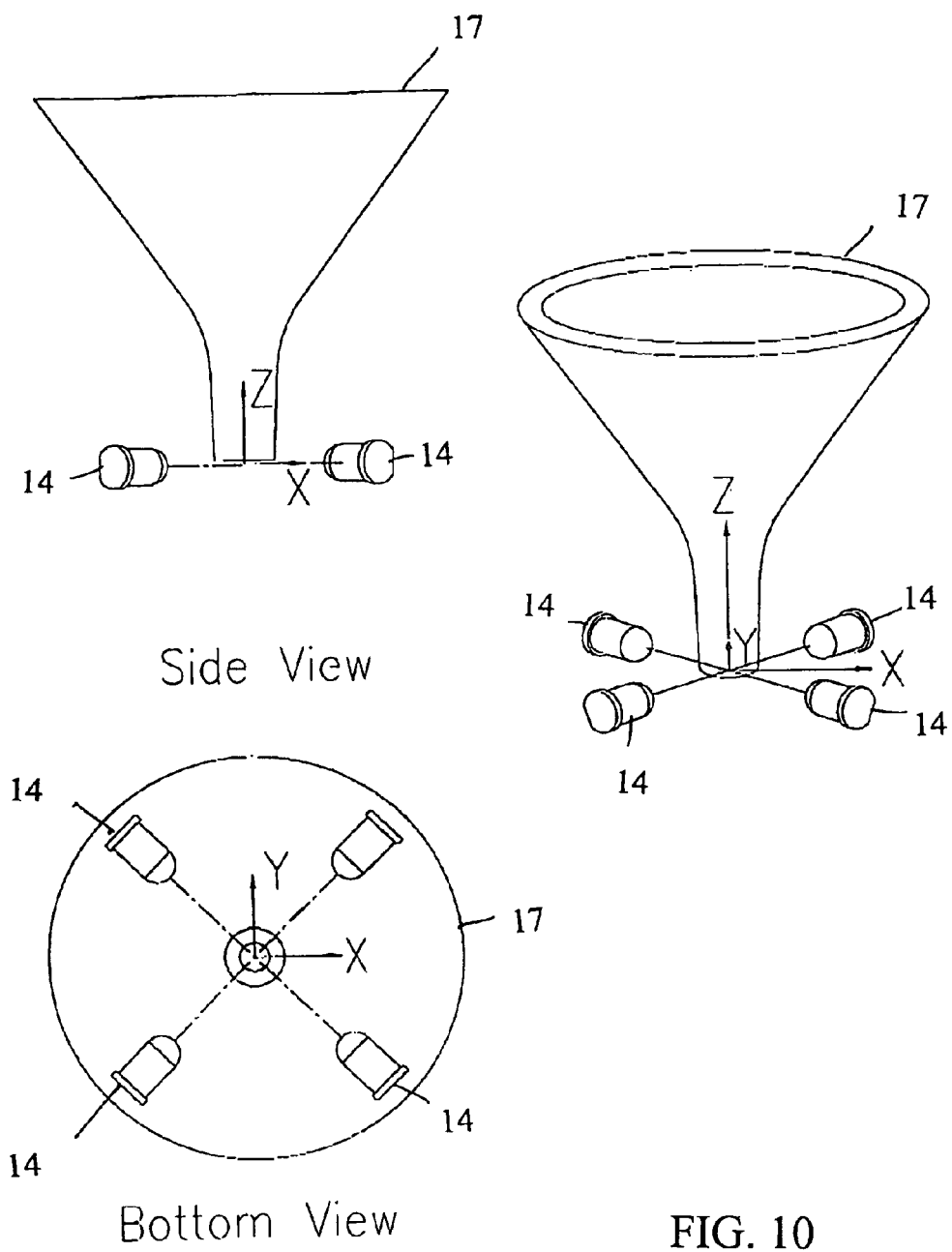
FIG. 10 is a drawing showing how two orthogonal infrared beams are oriented in a horizontal plane to intersect underneath the bottom opening of the funnel.

At least one beam transducer 14 is mounted in sensor head 24 at the bottom of the upper probe body section 13. Each transducer 14 is operatively connected to probe circuit board 34 either directly or through a transducer cable 25 such as is shown in FIG. 3. For purposes of the present invention, directly connected means the leads of the transducer connect to the circuit board. When two of more transducers 14 producing two or more beams are used, the beams can have any orientation which a falling object, such as an insect or grain particle, will pass through. When using multiple beams it is well within the ordinary skill in the art to determine beam orientation given the present detailed description, such as for example, vertically stacked beams which are parallel to each other; non-parallel beams; non-parallel intersecting beams; orthogonal, intersecting beams; etc. However, the different orientations and/or positions of multiple beams should improve the probability of capturing the largest cross-sectional area of the falling object. For purposes of the present invention, multiple beams means two or more beams. This is important because the orientation of a falling object is random—i.e., two objects that are the same will fall through a beam in different orientations and the probe could see them as differing in size depending on the orientation as it passes through a beam. To further refine the use of multiple beams, the use of orthogonal, intersecting beams allows the use of vector addition which combines the results obtained from the different beams and increases the accuracy of species identification. For sensors 20 having transducers 14 that produce three orthogonal, intersecting beams, the beams are oriented symmetrically about the vertical fall line through the funnel as the rotational axis of symmetry (FIG. 9). When two orthogonal, intersecting beams are used, the beams are located along a horizontal plane (FIG. 10). Probe circuit board 34 is mounted near transducer(s) 14 within a distance that results in an acceptable degradation of transducer 14 signals and susceptibility to electrically induced noise. One of ordinary skill in the art could readily determine the maximum distance for acceptable degradation of transducer 14 signals and susceptibility to electrically induced noise.

Figure 5A:
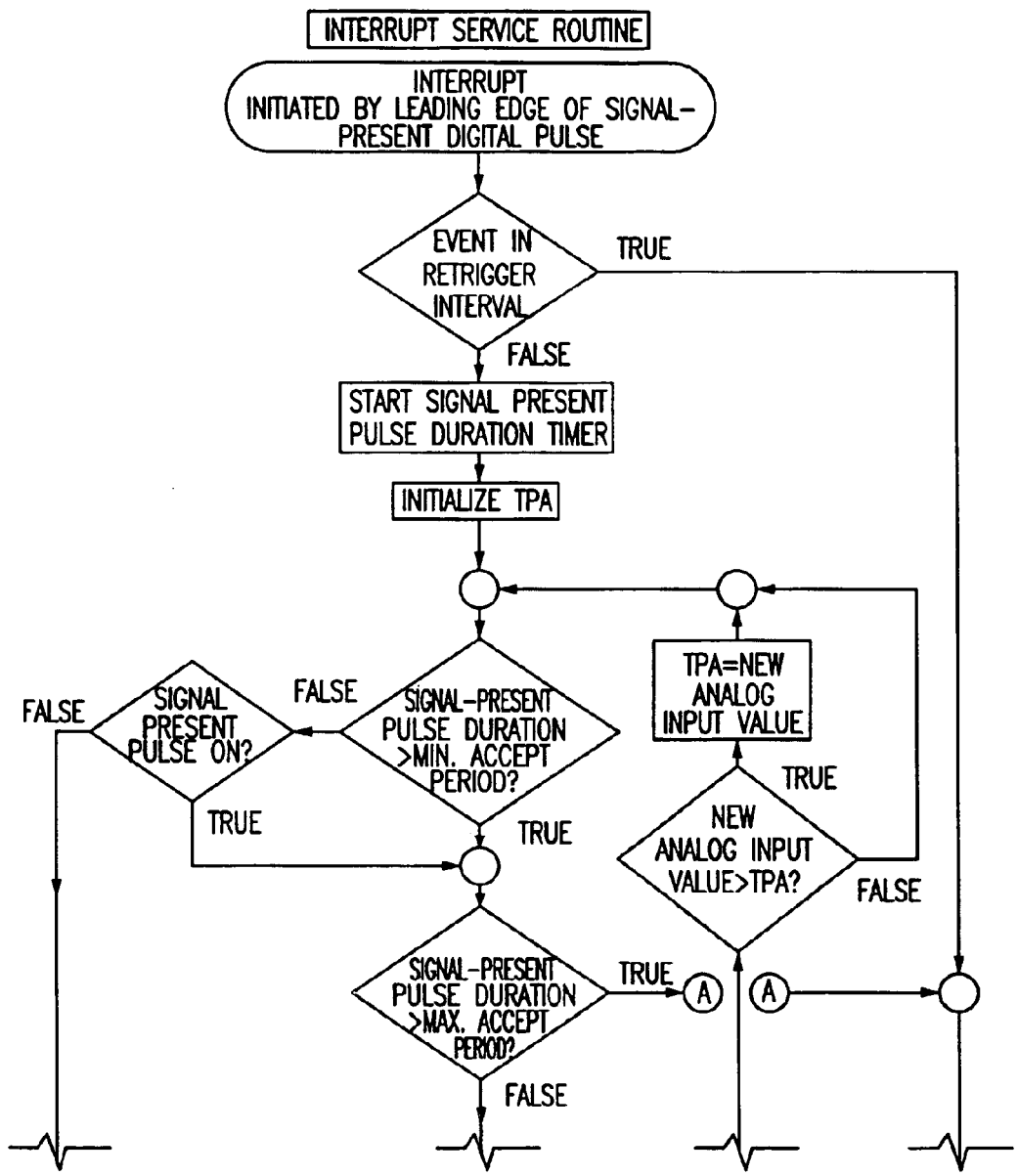
FIG. 5 is a flowchart of the microcontroller signal processing program sub-component when a single infrared beam is employed and part of the program's function is to check for adherence to signal timing criteria.
Figure 5B:
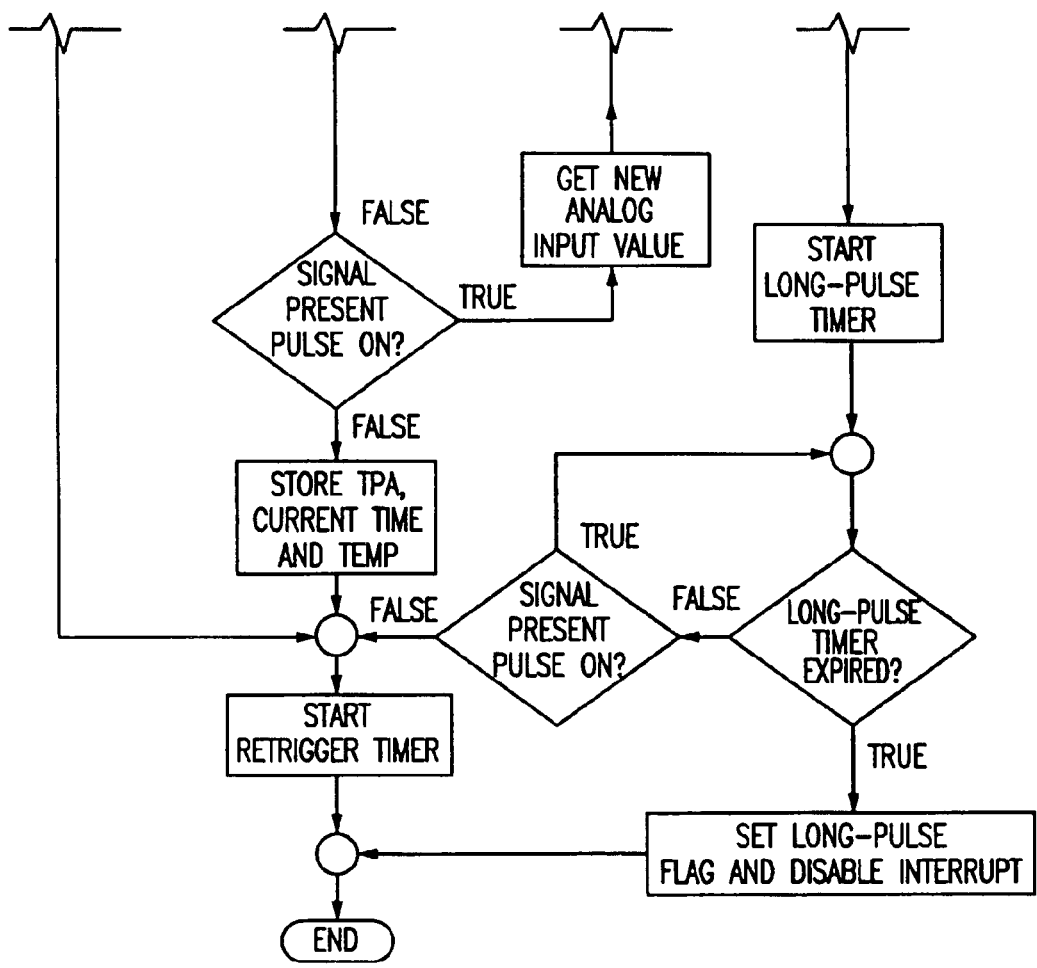
Figure 5C:
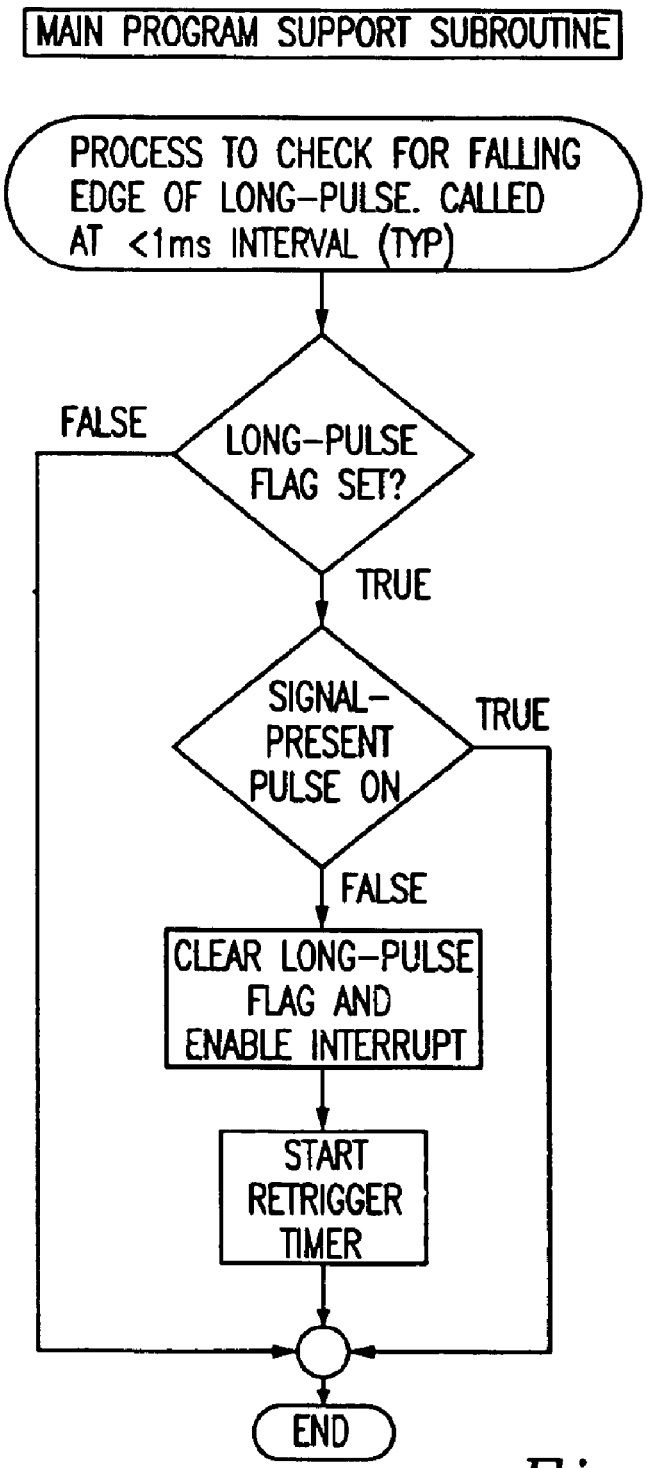
Figure 15A:
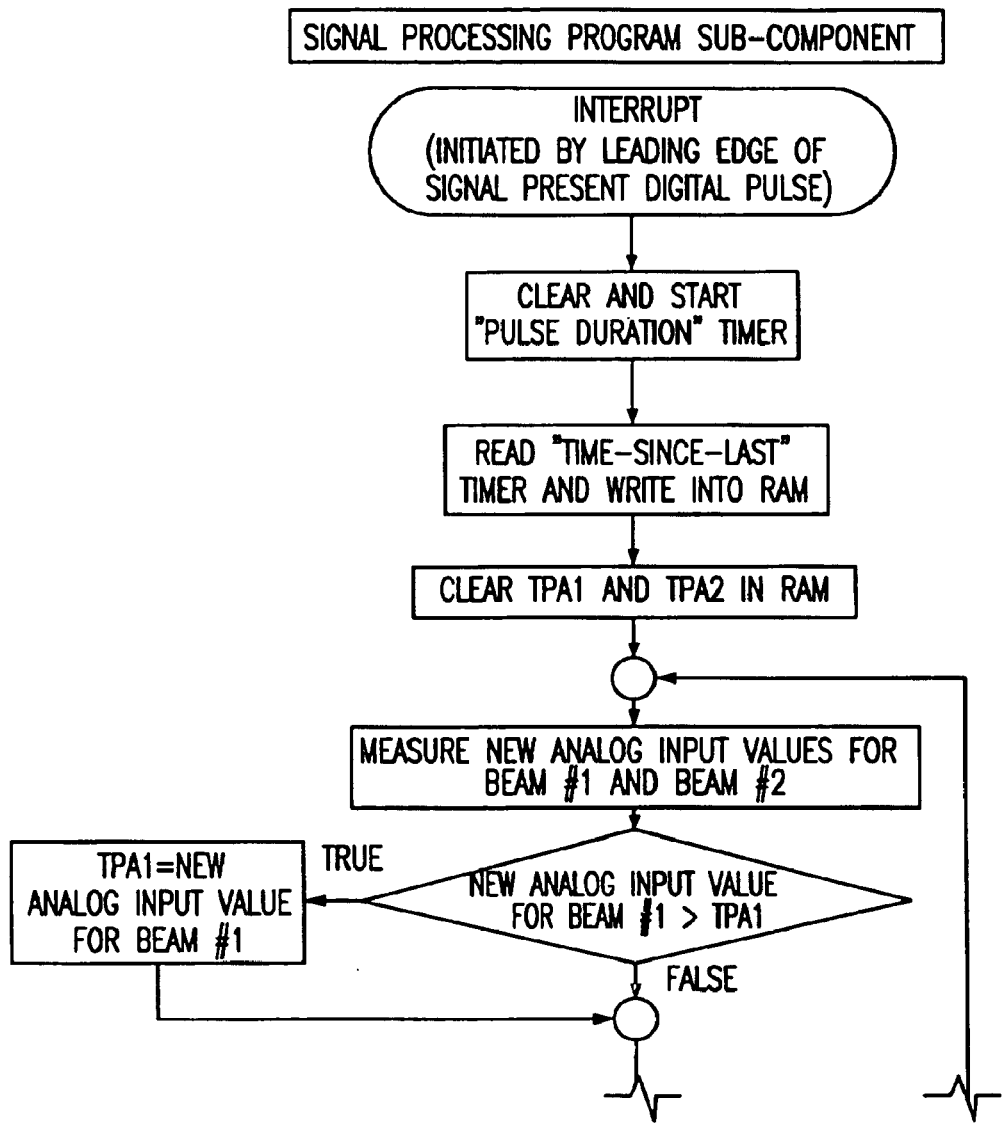
FIG. 15 is a flowchart of the signal processing program sub-component for a sensor 20 with two infrared beams when the timing criteria are checked by the central location device.
Figure 15B:
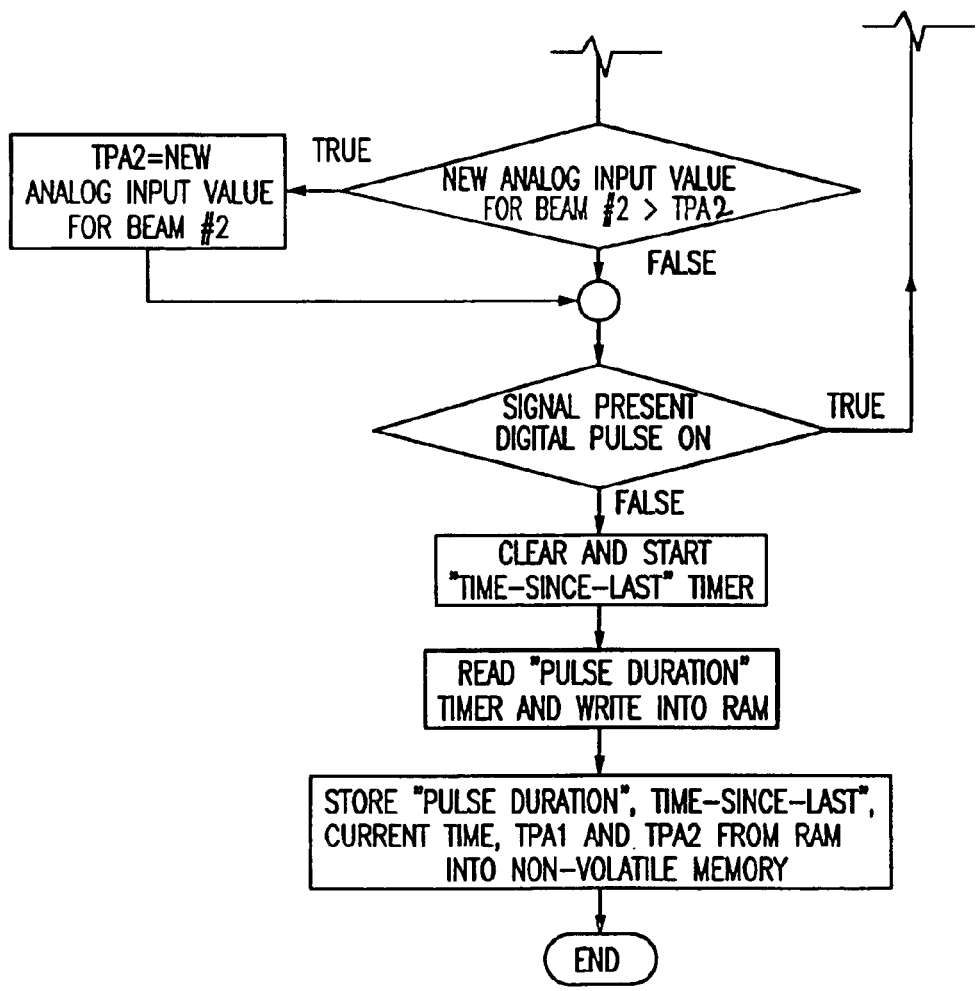
Figure 16A:
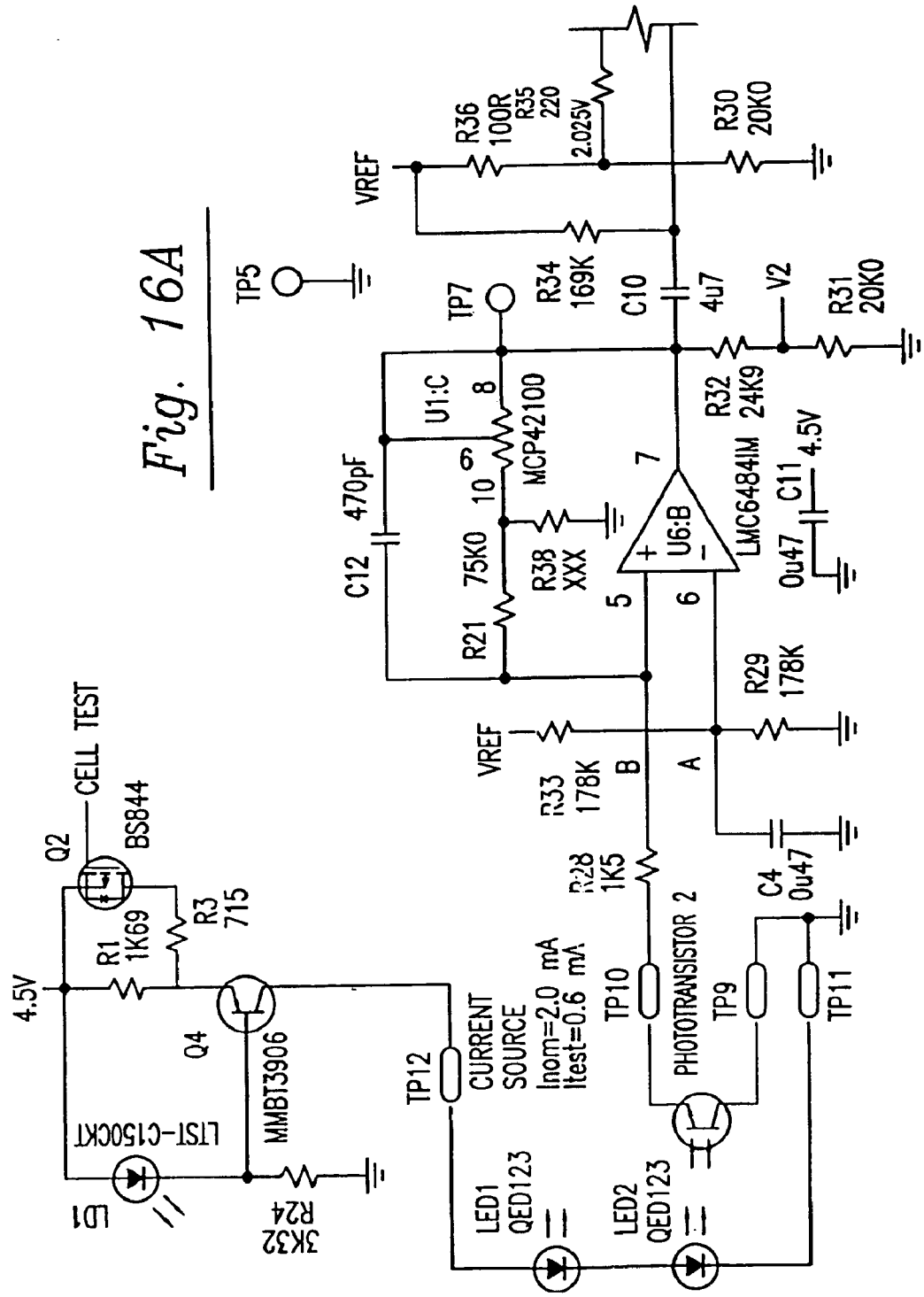
FIG. 16 is a detailed schematic of a probe circuit implemented with infrared transducers producing two beams.
Figure 16B:
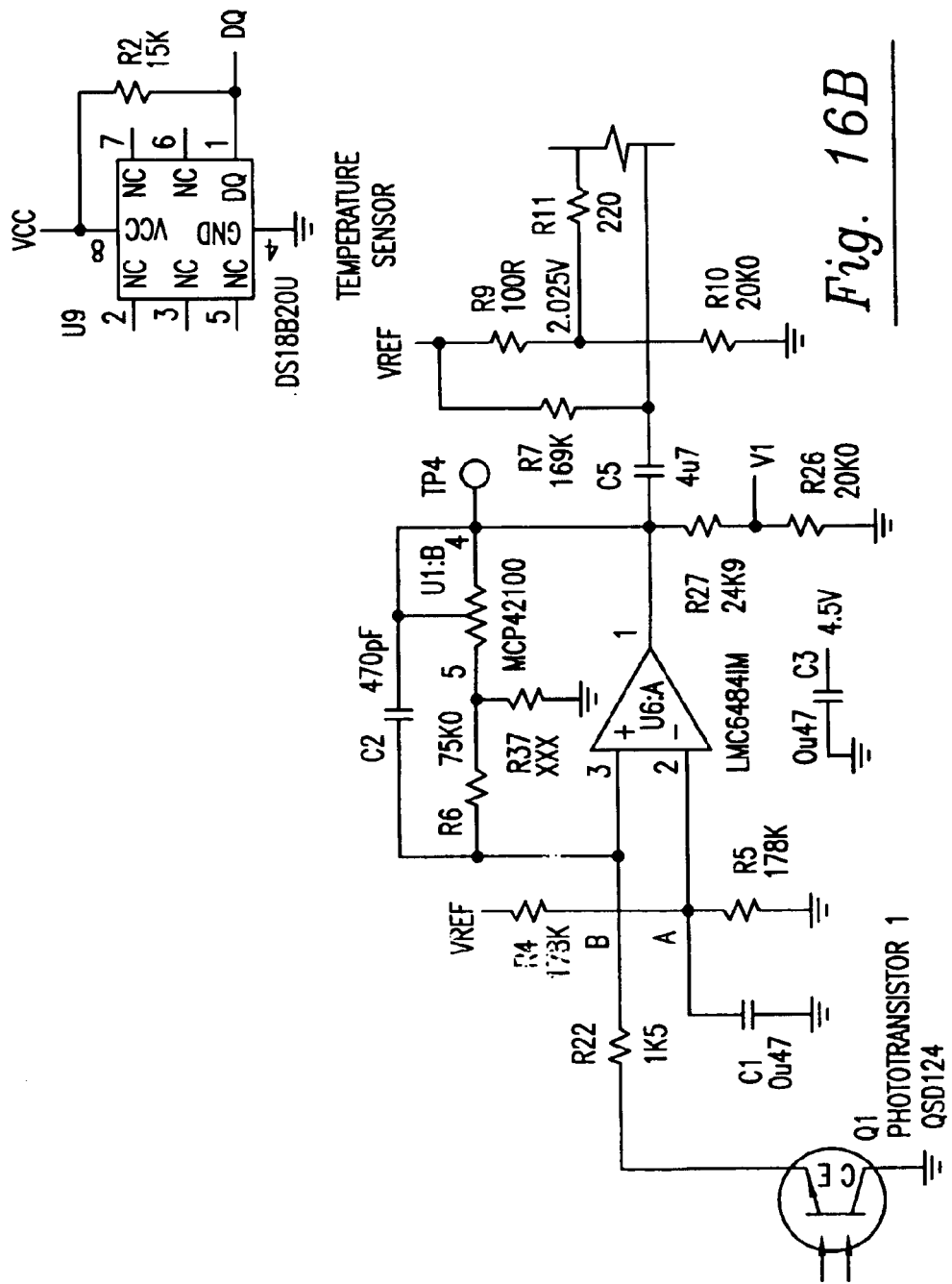
Figure 16C:
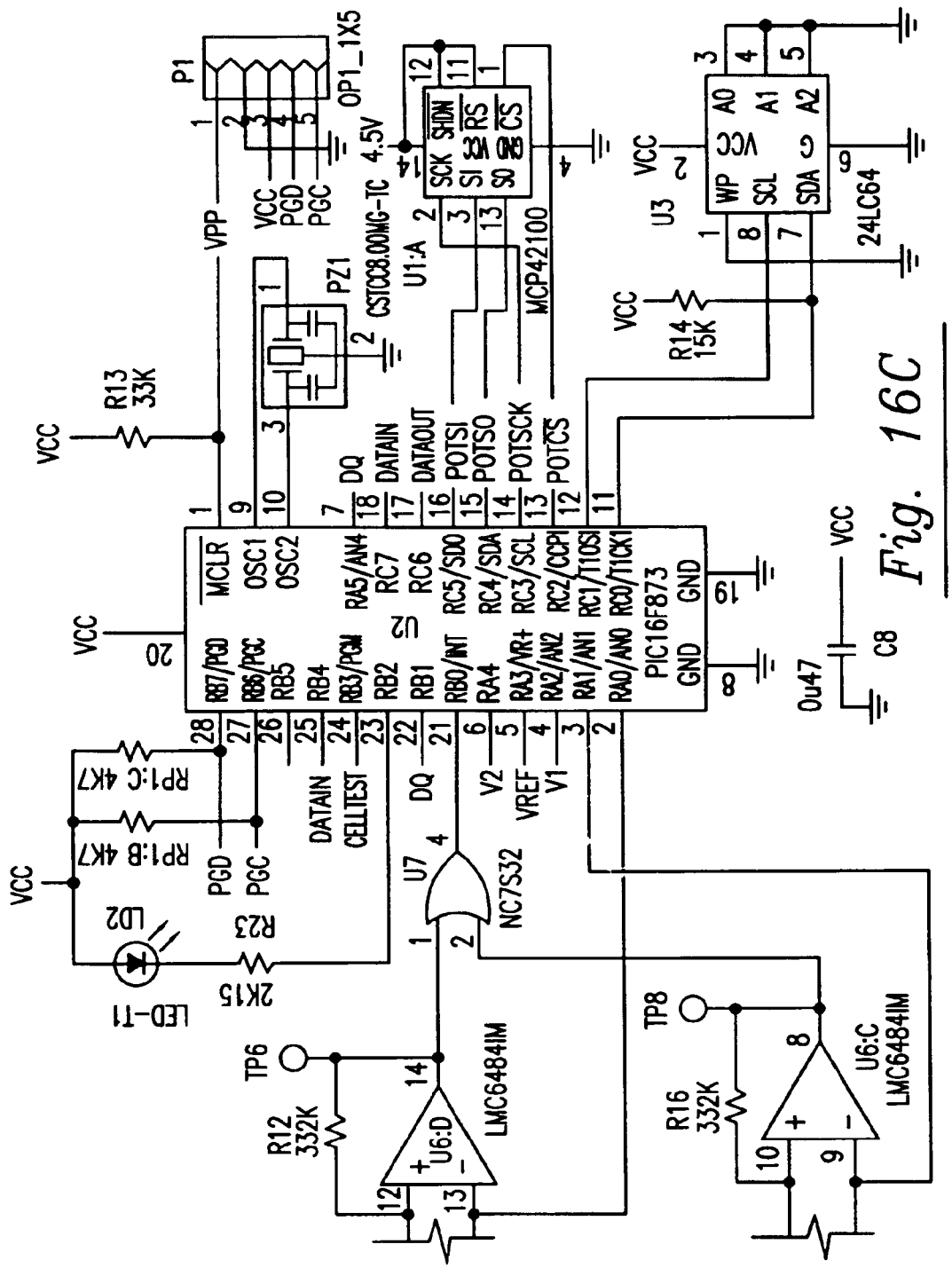
Figure 16D:
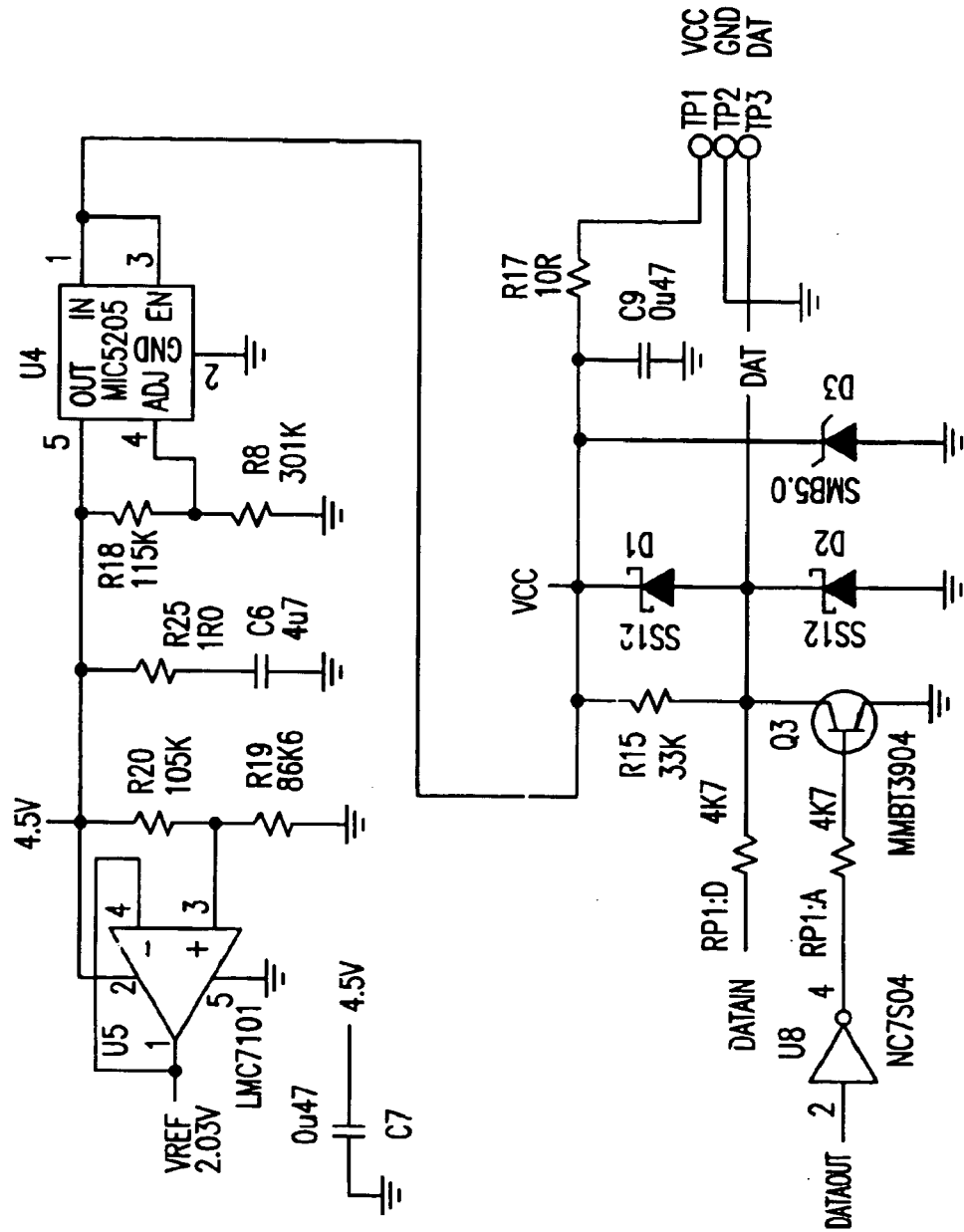

Circuit board 34 (FIGS. 2, 3, and 12) includes a programmable microcontroller 36 and at least one voltage threshold detector 40. It further includes beam current generator 35 which employs the supply voltage and series resistance to control the LED current. Alternatively, multiple LEDs can be connected in series and driven by a constant current source to provide greater current stability while permitting simultaneous self-testing by momentarily decreasing the output of the constant current source. Microcontroller 36 includes at least one analog input 44, at least one digital input 46, a digital output 48, and an internal nonvolatile memory 37 containing a software program for analyzing at least one signal. The software program measures the duration of a signal, the duration of time between signals, monitors the signal for a maximum analog value, records the time at object detection, and stores these extracted parameters for transmission to a central location device 42. The pulse timing decision making analysis software can either be located in microcontroller 36 or central location device 42. It is well within the ordinary skill in the art to determine where the decision making process is located. Some of the advantages of having the pulse timing decision analysis in central location device 42 include reducing the microcontroller software decision making overhead, allowing for a higher rate of insect counting; allowing criteria tuning based on experience where the user can select minimum and maximum allowable pulse durations and minimum allowable time between pulses; alerting the user of problems such as excessive electrical noise or insects loitering in the beam(s) which are indicated by excessive numbers of counts being rejected due to signal pulse data that do not satisfy the timing criteria; etc. The duration of the signal and the duration of the time between signals is determined by measuring the signal present digital pulse duration and the time between contiguous pulses (time-since-last) by the timers in microcontroller 36 running a signal processing software subcomponent. These timing data are used for decision making by either microcontroller 36 or central location device 42 (FIGS. 5 and 15). Each probe 12 with at least one transducer 14 producing at least one beam, has dedicated circuit board 34 which processes the transducer 14 output signal, stores the extracted parameter data in non-volatile memory 37, and on command, transmits this data back through a transmission medium 52 to central location device 42 (FIGS. 2 and 12). For purposes of the present invention, the non-volatile memory 37 is a computer readable medium. The computer readable medium must be capable of operatively interacting with central location device 42. External memory can be added to circuit board 34 if additional memory is needed for storing extracted parameter data prior to transmission to central location device 42. A transmission medium is any medium through which data can be transmitted such as for example cables, including fiber optic cables; wireless, including radio links; etc. When probes 12 contain a temperature sensor 33 (FIGS. 2 and 3), a temperature reading is stored in a memory such as memory 37 of microcontroller 36 or external memory located on circuit board 34, each time an insect is detected and/or on scheduled intervals. This data is also transmitted with probe 12 extracted parameter data in order to aid in using the data to estimate infestation levels. For the purposes of this invention, the central location device 42, by way of definition, is anything which can acquire, analyze, store, and display data, such as for example a computer, a hand-held monitor, etc. The data can be displayed as text or graphically to enhance the observation of trends.

Figure 6A:
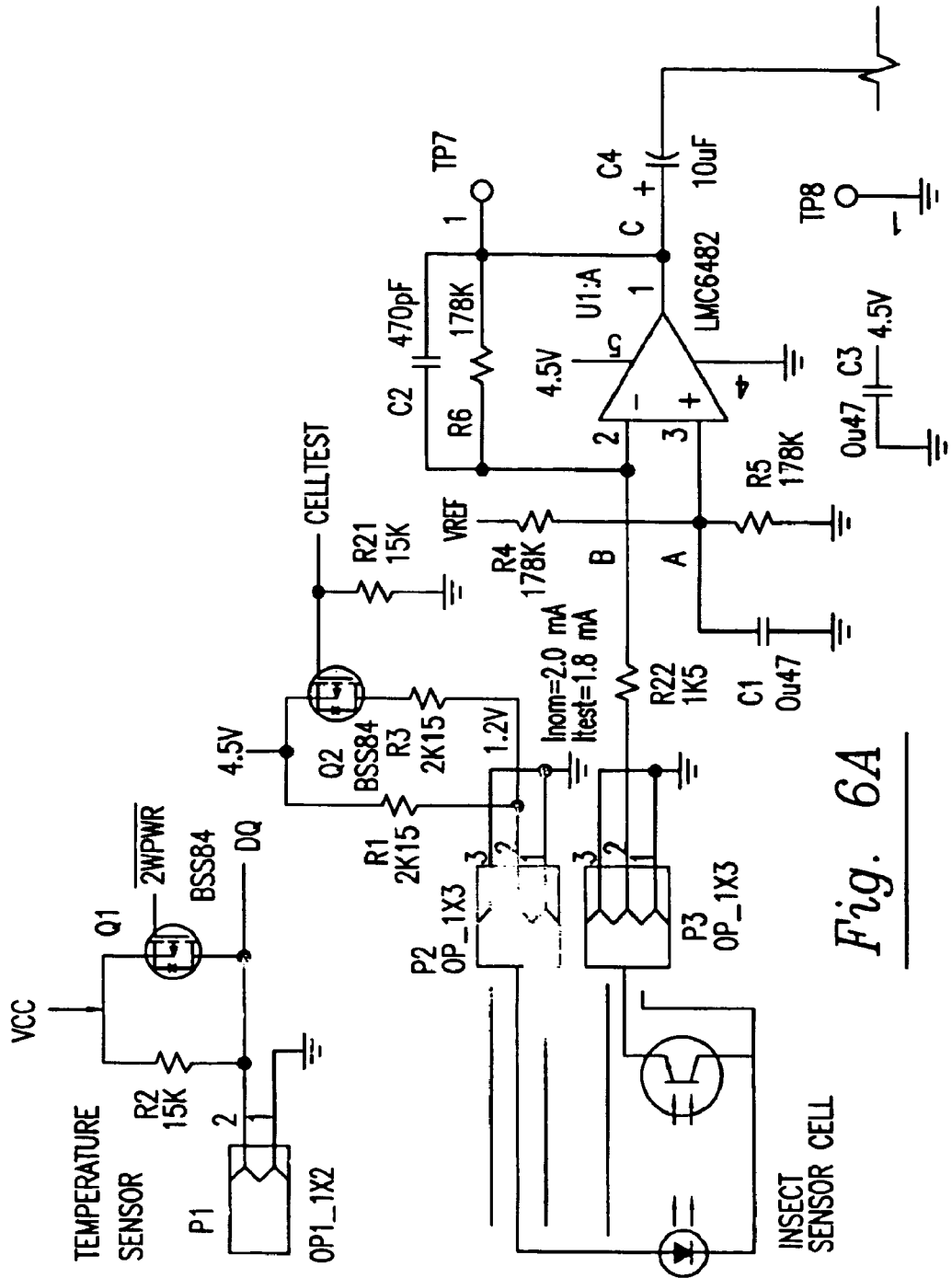
FIG. 6 is a detailed schematic of the probe circuit implemented with infrared transducers producing a single infrared beam.
Figure 6B:
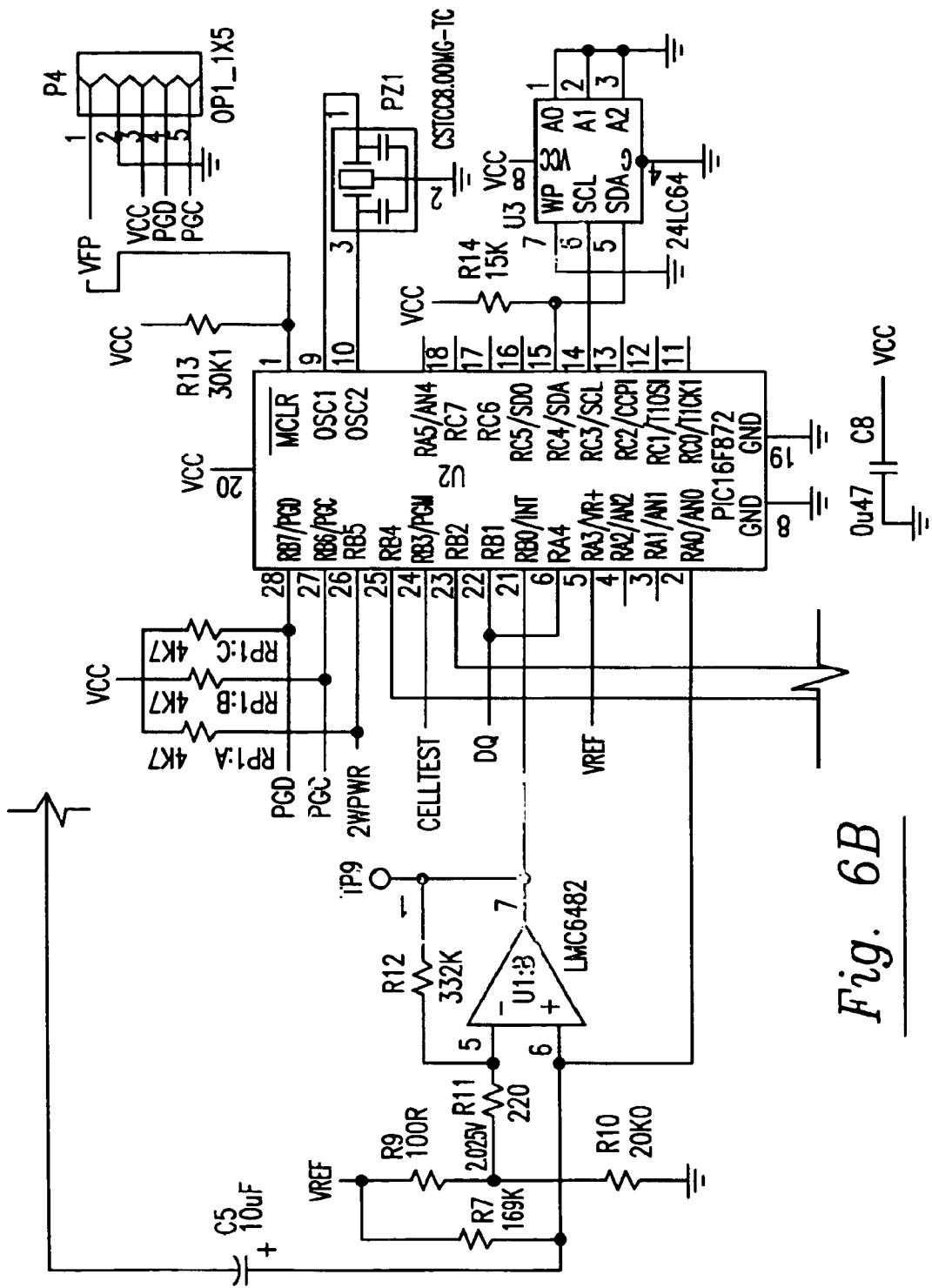
Figure 6C:
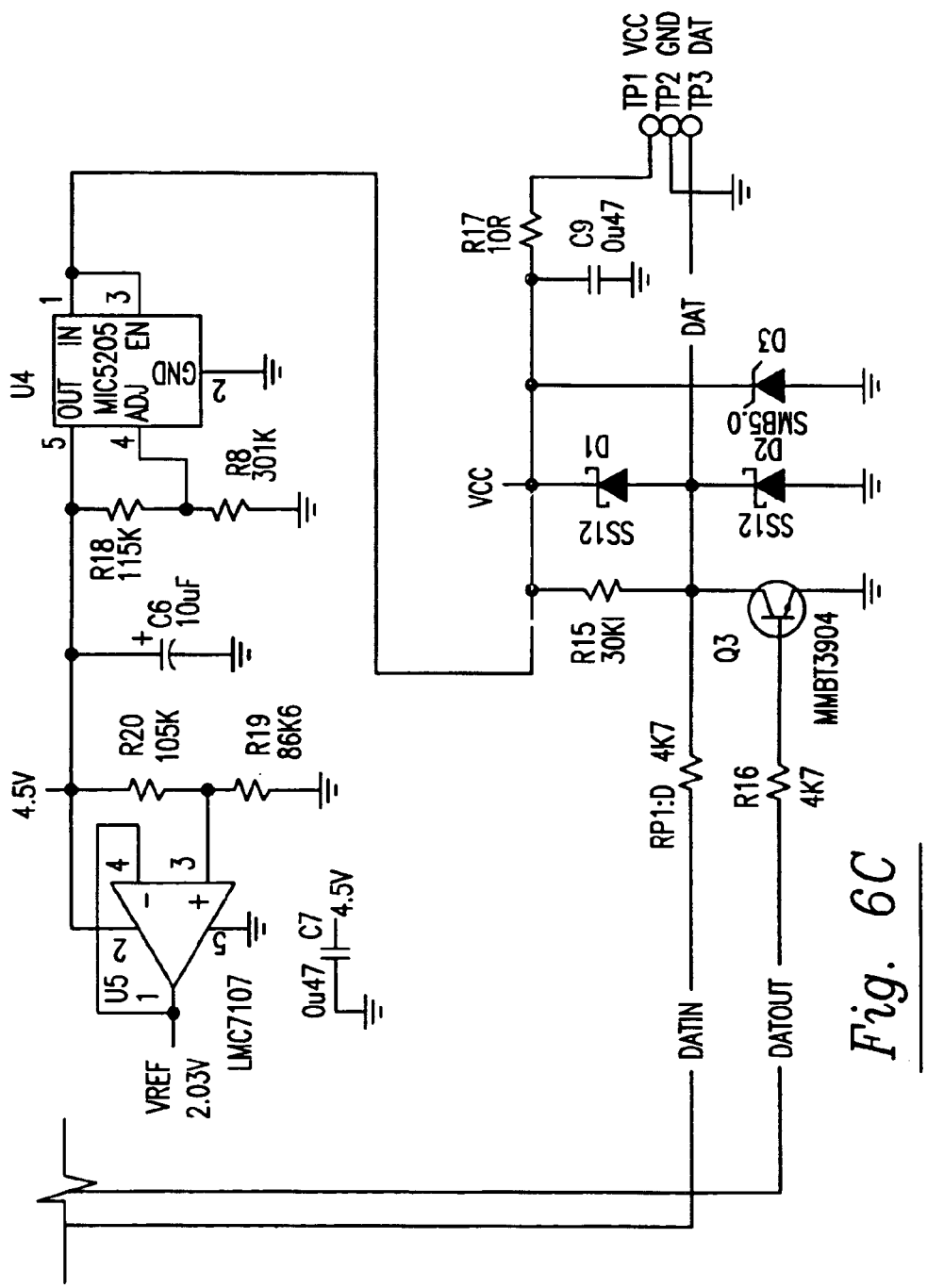

In operation of circuit board 34, the conditioned sensor output is connected to the various parts of board 34 via at least one capacitive coupling 39 in order to present a signal to coupling 39 only when a sensor output transient occurs as when an object passes through a beam or beams. For purposes of the present invention, sensor output is conditioned by an operational amplifier configured as a current-to-voltage convertor 38. This conditioning circuit implementation allows the phototransistor 32 bias voltage to be set by the bias reference voltage 41 applied to the operation amplifier. The capacitive coupling and this phototransistor bias circuit effectively eliminates the effects of slow changing sensor output signals due to such variables as changing environmental conditions and/or sensor component aging. Microcontroller 36 has at least one analog input 44 (analog to digital converter; A/D input) and a non-volatile memory 37 as well as digital inputs 46 and outputs 48 (FIGS. 2 and 12). The capacitively coupled sensor analog voltage signal is applied to analog input 44 as well as to a voltage threshold detector 40. For example, see FIG. 6, Pin 2 of PIC16F872 for a single beam and FIG. 16, Pins 2 and 3 for two orthogonal, intersecting beams in a horizontal plane. The threshold level of detector 40 is set slightly above the electronic noise floor of the conditioned sensor voltage signal so that it generates a signal present digital pulse (FIG. 4) whenever any object passing near the transducer 14 alters the transducers' 14 output level. This signal present digital pulse, which persists as long as the sensor signal is greater than the threshold level, is connected to digital inputs 46 (FIGS. 2 and 12) of microcontroller 36 to alert it to begin processing the signal coming in on its analog inputs 44. Also see FIGS. 6 and 16, Pin 21 of PIC16F872 and PIC16F873 for a single beam and two orthogonal, intersecting beams in a horizontal plane, respectively. The signal present digital pulse is also monitored by microcontroller 36 to determine the duration of a signal and duration of time-since-last signal. Microcontroller 36 stores the data extracted from sensor signals in its memory 37 and, upon request from a central location device 42, transmits this data back to it using a serial transmission protocol (FIGS. 2 and 12) For a single beam or two orthogonal, intersecting beams in a horizontal plane, for example, these are transmitted back via Pin 23 of PIC16F872 or PIC16F873, respectively (FIGS. 6 and 16) Multiplexer 50 allows the single transmission channel 52 to be bidirectional, carrying both the data request from central location device 42 to microcontroller 36 and stored extracted parameter data in the opposite direction.

Figure 7:
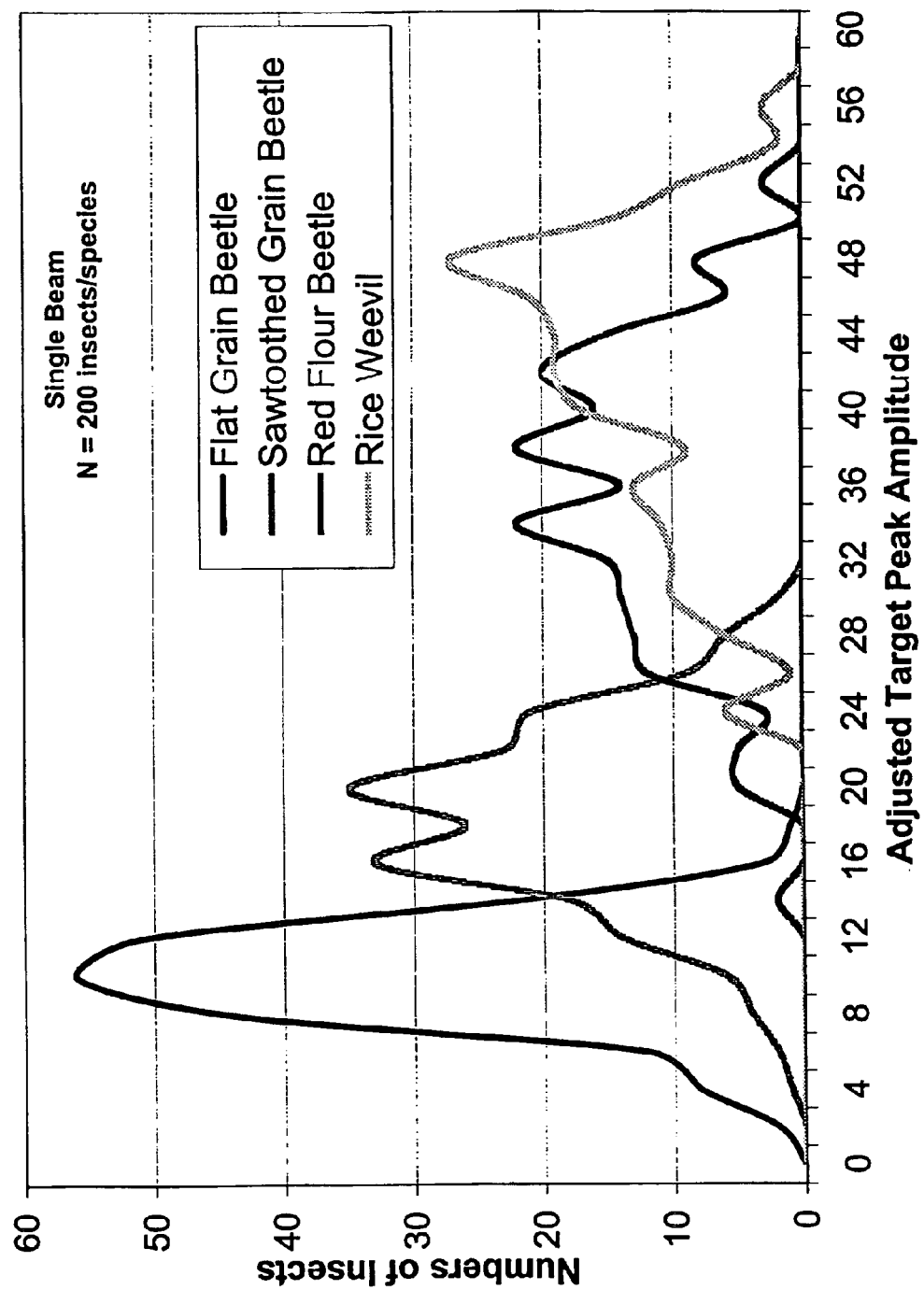
FIG. 7 is a graph of pulse amplitude distributions for four different insect species as obtained with a single infrared beam.
Figure 13:
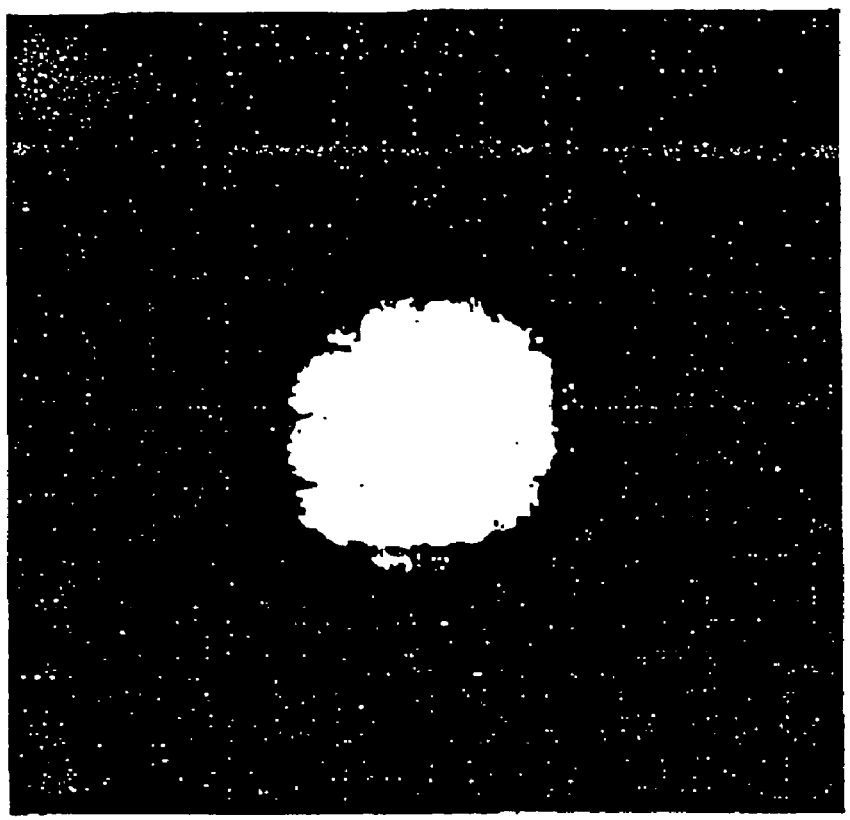
FIG. 13 is a photograph of the beam generated by an infrared LED and projected from a distance of about 7.6 mm onto a sheet of graph paper with about 1 mm grid spacing, showing its nonuniform intensity.

The sensor output analog processing microcontroller software programs are written into the probe circuit at the time of manufacture of each probe after the circuit is completely assembled. The software programs include a signal processing subcomponent, a calibration sub-component, and a data transmission sub-component embedded in a main program loop. The signal processing sub-component operation is summarized in software flowcharts (FIGS. 5 and 15). It contains an interrupt service routine that is called by the main program to analyze the incoming sensor signal whenever the leading edge of an incoming signal present digital pulse generates an interrupt via the digital input 46 (FIGS. 2 and 12). See FIGS. 6 and 16, PIN 21 of 16F872 or 16F873 for a single beam or two orthogonal, intersecting beams in a horizontal plane, for example. A signal present digital pulse usually indicates that an insect is falling past at least one transducer 14. The falling insect simultaneously results in a sensor analog voltage signal applied to the analog input 44 of microcontroller 36, whose instantaneous amplitude is at least partially determined by some physical property of the insect indicative of its species as sensed by the at least one transducer 14. The interrupt service routine monitors the analog sensor signal during the presence of the signal present digital pulse, and stores the maximum analog value attained during the signal present digital pulse interval and its time of occurrence (time-stamp). This stored value is called the Target Peak Amplitude (TPA) of the analog signal, and it is achieved during the excursion of the insect past the at least one transducer 14. It is statistically proportional to some physical property of the insect. However, there can be a significant variability in the distribution of these Target Peak Amplitudes obtained when multiple insects of the same species fall past the at least one transducer 14. In the case of using infrared beam transducers, the nonuniform cross-sectional intensity of the infrared beam (FIG. 13), the nonuniform cross-sectional sensitivity of the phototransistor 32, and the random orientation and pathway of insects as they pass through the beam, all contribute to the variability in these Target Peak Amplitude distributions (FIG. 7). Since these distributions for different insect species may overlap, it may not be possible to positively identify the species of each falling insect by the Target Peak Amplitude of its generated analog signal using a single beam. Even so, when a number of insects of the same species falls past a transducer 14, a distribution pattern emerges with a mean and variance that can be used to identify that species. In those situations where the identity of the species cannot be ascertained with absolute certainty, it can be narrowed down to those with similar physical properties, such as similar body size as in the case of an infrared beam. It then may be narrowed down even further by knowing the predominant species in a particular geographic region. The validity of this statistical approach is based on empirical evidence that stored-product insects of any one species tend to aggregate in clusters so that the vast majority of insects entering a particular probe during a limited time interval will be of the same species. Even if there is still uncertainty, there may still be enough information to make insect control management decisions without visual inspections of the infested commodity since the destructive potential of different species is generally proportional to their body size.

Figure 8:
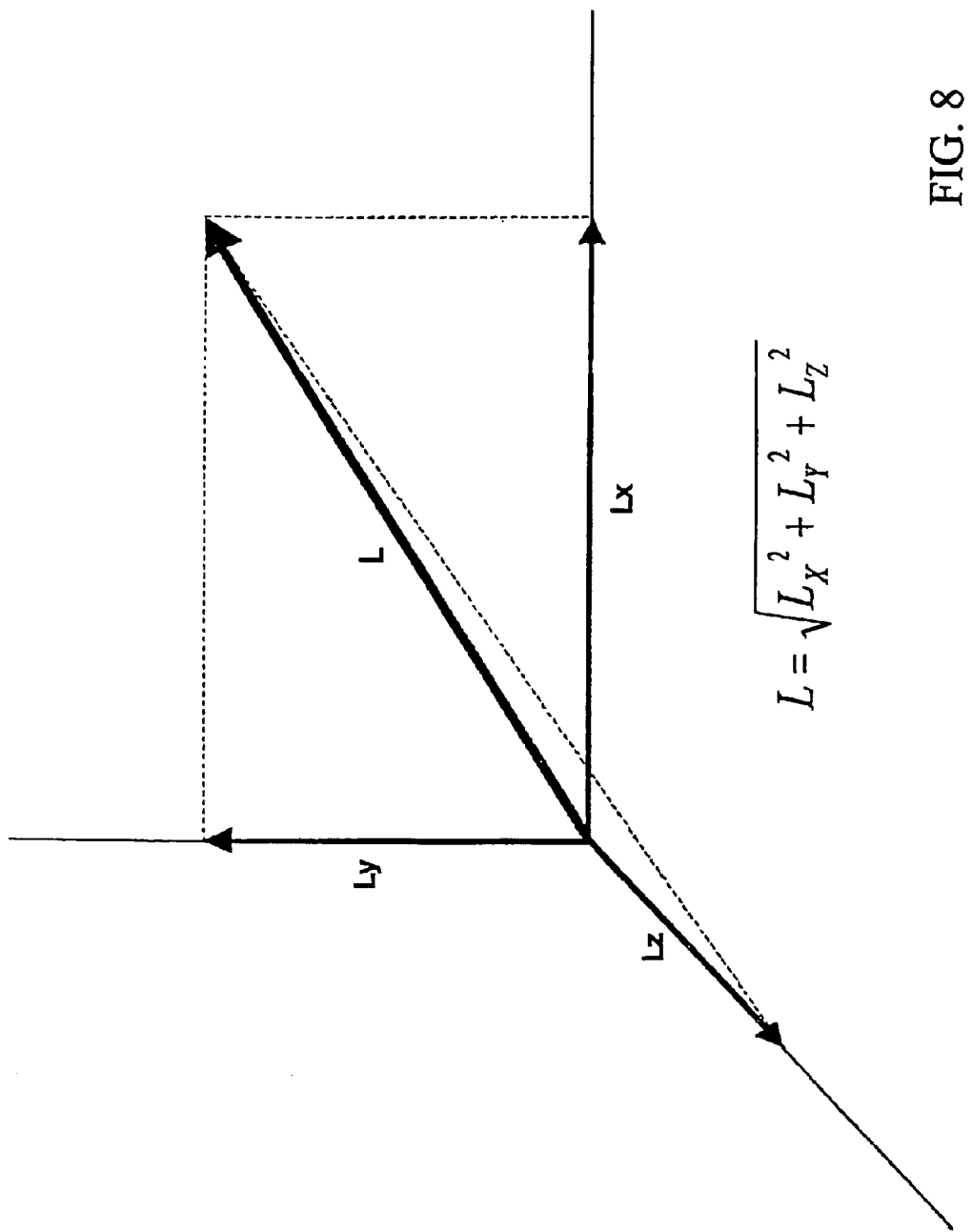
FIG. 8 is a graph showing how the length of a line L with any orientation in three-dimensional space can be calculated from the length of its projections on the three orthogonal coordinate axes.
Figure 11:
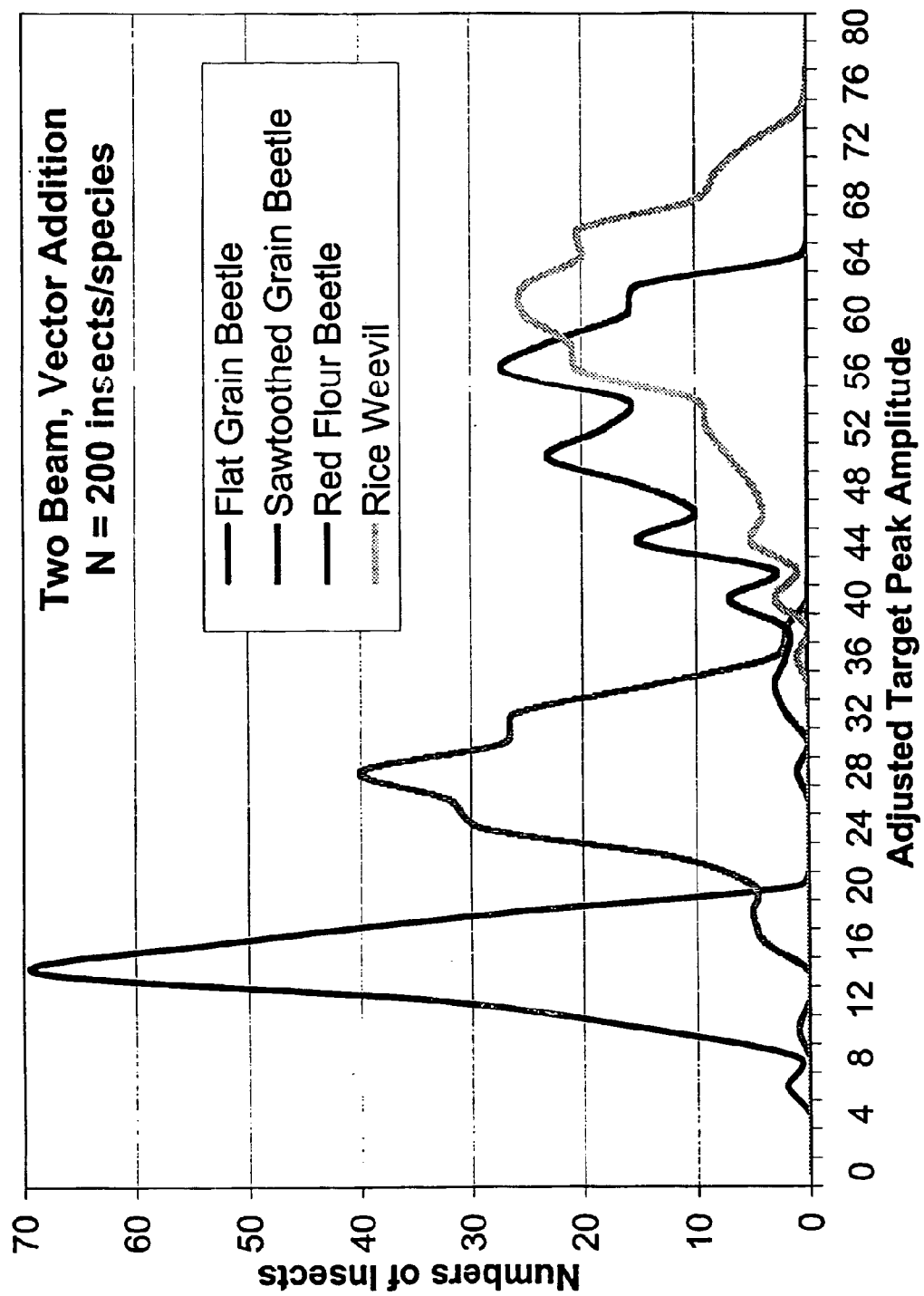
FIG. 11 is a graph of pulse amplitude distributions for four different insect species as obtained with two intersecting, orthogonal infrared beams. The overlap of the distributions is far less than that obtained with a single beam as shown in FIG. 7.

When three orthogonal, intersecting beams are used, the three pulse amplitudes can be used to calculate an effective insect size value that is virtually independent of a falling insect's orientation. This calculation is the vector sum of the three pulses' amplitudes and is equal to the square root of the sum of the squares of the three pulse amplitudes. As an analogy of this (FIG. 8), if a line segment of length L with any orientation in 3 dimensional space is viewed along each of the three orthogonal coordinate axes (x, y, and z), the exact length of the segment can be calculated as the square root of the sum of the squares of the length of the segment as projected (seen) on each of the coordinate axes. Thus, the variability of the above effective insect size value would then be mainly due to factors other than insect orientation, such as non-uniformity of the infrared beams' intensities. With the use of only two orthogonal, intersecting beams, the pulse peak amplitudes from the two beams are utilized by taking the square root of the sum of the squares (vector sum) of the two amplitudes which is a more accurate method than the use of a single beam implementation for statistically inferring the species of a falling insect (FIGS. 7 and 11). Each beam has its own current-to-voltage converters 38, capacitive coupling 39, and voltage threshold detector 40 as described above. Microcontroller 36 has two A/D inputs 44, one for each beam, and the individually measured pulse amplitudes are both transmitted back to central location device 42.

Since the signal present digital pulse is generated whenever any object passes near the at least one transducer 14 producing at least one beam, objects other than stored-product insects of concern will also get recorded. However, since their Target Peak Amplitudes are recorded, detections of differing sized objects will not erroneously be counted as stored-product insects of concern, such as for example, weevils or beetles. In fact, these other counts may provide useful information about the presence of other differing sized targets such as, for example, mites, psocids, predator insects, grain particles, etc.

When there are multiple signal present digital pulses (overlapping but not necessarily simultaneous) generated as an object falls through the intersection of multiple beams, the timing of the multiple signal present digital pulses can be processed individually, both in terms of their durations and the time intervals between pulses. However, the microcontroller 36 is alerted to begin processing at the arrival of the earlier analog pulse by combining together the multiple signal present digital pulses using a logical OR Gate 36 (FIG. 12) whose output is connected to the single interrupt generating digital input 47 of microcontroller 36 (FIG. 12). In addition, the individual signal present pulses are also connected to other digital inputs 46 allowing for their possible utilization. The resulting composite signal present digital timing pulse, which begins at the leading edge of the earliest individual signal present pulse and ends at the trailing edge of the latest individual signal present pulse, is used to generate the microcontroller interrupt.

The duration of the signal present digital pulse is used to discriminate between falling objects and false detections. Optionally, this function can either be included in the microcontroller 36 interrupt service routine or in the central location device 42 software. Since the range of time it takes for an object to fall past at least one transducer 14 is known, microcontroller 36 is programmed to not record events when the signal present digital pulse durations are not within some known range in order to prevent false positives (erroneous counts). For example, since the range of time it takes for an object to fall through an infrared beam is known to be greater than about 2 msec and less than about 30 msec, either microcontroller 36 is programmed to not record events when the signal present digital pulse durations are outside of this range in order to prevent false positives or central location device 42 is programmed to flag false positive events based on the above (user adjustable) timing criteria. Electrical transients or noise spikes, that may be generated by electric machinery or electronic current surges, are typically a few microseconds in duration and almost always less than about 1 msec. Therefore, they would not be recorded (microcontroller 36) or would be flagged (central location device 42) despite the fact that their Target Peak Amplitudes may be comparable to those produced by falling insects. Also, in the unlikely event that an insect is able to loiter in the vicinity of the at least one transducer 14 or by crawling onto the surface of the transducer(s) 14, a series of false signal present digital pulses may be generated. However, these are almost always greater than some known time duration (30 msec) and would therefore not be recorded. This function can also be handled by central location device 42 by flagging events outside the timing criteria. To provide additional protection against false positives due to loitering insects, microcontroller 36 or central location device 42 is programmed to not record (microcontroller 36) or to flag (central location device 42) any signal present digital pulse generated within a specified retrigger interval (a time-since-last criteria with a default value of about 100 msec) of the end of a previously generated signal present digital pulse, even if the previous signal present digital pulse's duration was not within the acceptable range and therefore not recorded or was flagged. These default times can be optimized as the system is in use if the user sees that a different time frame will provide more accurate results. This retrigger interval also prevents multiple detections from being counted when a single insect falls past the at least one transducer 14, either due to an irregular (double peaked) shaped analog waveform or due to grain particles being pulled in by the insect when it enters a probe.

The above features are accomplished by the signal processing sub-component as shown in the software flowcharts (FIGS. 5 and 15) for when the timing decision criteria are checked in microcontroller 36 or in the central location device 42, respectively. In the flowchart of FIG. 5, when the leading edge of an incoming signal present digital pulse generates an interrupt, the interrupt service routine first checks whether the interrupt is within the retrigger interval from the end of the preceding signal present digital pulse. In the non-retrigger case where a signal present digital pulse begins sufficiently after any previous falling insect, the interrupt service routine moves down the central column shown in the flowchart. The interrupt service routine first starts a signal present digital pulse duration timer and sets an initial Target Peak Amplitude value. It then enters an analysis loop where it begins by checking the signal present digital pulse duration timer. If the elapsed time is less than a known minimum acceptable period (sensor specific) and the signal present digital pulse is no longer present (indicative of a noise spike), then the interrupt service routine drops out of the analysis loop, the retrigger interval timer is started, and the interrupt service routine ends. If not, the interrupt service routine continues down the central column and again checks the signal present digital pulse duration timer. If the elapsed time is greater than a known maximum acceptable period (indicative of a crawling insect), then the interrupt service routine drops out of the analysis loop and a long-pulse timer (discussed below) is started. If not, the interrupt service routine continues down the central column and checks for the presence of the signal present digital pulse. If the signal present digital pulse is still present, then the interrupt service routine reads the current value of sensor analog voltage signal and compares it with the stored Target Peak Amplitude value. If the current value is larger, then it becomes the new Target Peak Amplitude value, or else the previous Target Peak Amplitude value remains. In either event, the interrupt service routine returns back to the beginning of the analysis loop where it previously checked the signal present digital pulse duration timer for some minimum acceptable period elapsed and the process repeats itself. If the signal present digital pulse ends while the interrupt service routine is going around the analysis loop (indicative of an insect falling past the transducer 14 within the acceptable time range), it drops out in the central column to store the Target Peak Amplitude, current time, and temperature. Then the retrigger interval timer is started and the interrupt service routine ends.

In the retrigger case of an object falling past a transducer 14 in less time than the retrigger interval after a previously falling object, indicating that the incoming analog waveform should be ignored, the central column of the signal processing routine is bypassed and the long-pulse timer is begun. The function of this timer is to prevent an extremely long signal present digital pulse (e.g., due to a crawling insect) from tying up microcontroller 36 and preventing it from accomplishing its other tasks such as staying in communication with central location device 42. If the signal present digital pulse lasts less than the time-out duration of the long-pulse timer, then the retrigger interval timer is started and the interrupt service routine ends, or else a long pulse flag is set which disables further interrupts, and then the interrupt service routine ends. The long-pulse timer insures that the maximum duration of the interrupt service routine (which occurs in the non-retrigger case when the maximum acceptable period in the analysis loop is followed by a time-out of the long-pulse timer) is limited. A support subroutine (shown in the flowchart), which is regularly called by the main program while performing its other tasks, checks for the continued presence of an ongoing signal present digital pulse (i.e., a signal present digital pulse that continues beyond the end of the interrupt service routine it initiated) whenever the long pulse flag is set. Once an ongoing signal present digital pulse ends, the support subroutine clears the long-pulse flag (which re-enables interrupts), starts the retrigger interval timer, and microcontroller 36 is again ready to receive input signals from the transducer(s) 14.

When the decision criteria are checked in the central location device 42, the signal processing sub-component of the microcontroller software is substantially simplified. FIG. 15 shows the flowchart for this sub-component when two infrared beams are employed. When the leading edge of an incoming composite signal present digital pulse generates an interrupt, the interrupt service routine clears and starts the "signal present pulse duration" timer, reads the "time since last" timer (referred to as the "retrigger" timer in FIG. 5) and stores its value into temporary RAM. It then clears (initializes) the two Target Peak Amplitude values stored in temporary RAM. The interrupt service routine reads the current values of sensor analog voltage signals for both beams. The interrupt service routine then compares the current value with the stored Target Peak Amplitude value for beam #1. If the current value is larger, then it becomes the new Target Peak Amplitude value for beam #1, or else the previous Target Peak Amplitude value remains in RAM. The interrupt service routine then repeats this update process for beam #2. Afterwards, if the signal present digital pulse is still present, then the interrupt service routine loops back and again reads the current values of sensor analog voltage signals for both beams. This process continues until the composite signal present digital pulse is no longer present. At that time the interrupt service routine clears and starts the "time since last" timer, and then reads the "signal present pulse duration" timer and stores its value into temporary RAM. Finally the interrupt service transfers the "signal present pulse duration" value, the "time since last" value, and the two Target Peak Amplitude values from RAM into non-volatile memory (to be later read by central location device 42) and then the service routine ends.

The function of the calibration sub-component of the microcontroller program is to help provide consistent performance across probes despite large component tolerances and varying environmental conditions over longtime usage. Consistent qualitative performance is of importance since the values of the Target Peak Amplitudes will be utilized to make management decisions instead of just the quantitative insect count response. The calibration sub-component consists of two different response sensitivity initialization routines and then ongoing self-tests. Newly manufactured probes have an initial range of response sensitivity due to component tolerances, especially transducer 14 component parameters and sensor head mechanical tolerances. The first initialization procedure, performed with each new probe, consists of dropping a calibration basic object multiple times through the exact center of sensor head 24. The Mean of the Basic target Peak Amplitudes (MBPA) from these drops is permanently recorded in the non-volatile memory 37 of microcontroller 36 as a calibration factor. Whenever a probe is put into service and it establishes communication with central location device 42, it transmits its stored Mean of the Basic target Peak Amplitude value. There it is used to adjust the incoming Target Peak Amplitude data from that probe before they are stored and displayed. This normalization is accomplished by dividing the incoming Target Peak Amplitudes by the Mean of the Basic target Peak Amplitude, thus making all new probes appear to have identical sensitivity response performance.

Figure 14:
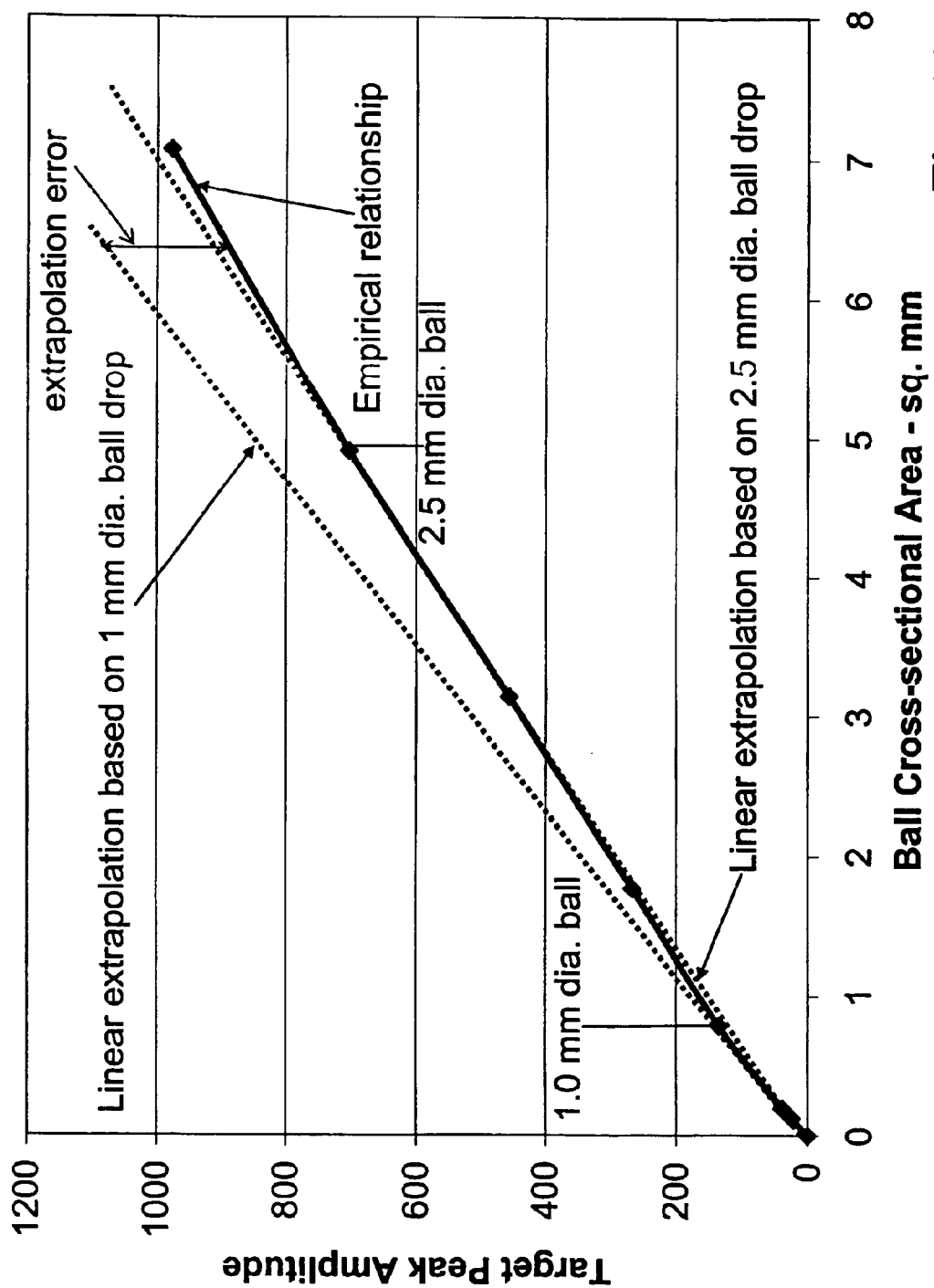
FIG. 14 is a graph of the empirically derived nonlinear relationship between Target Peak Amplitude and object cross-sectional area shown with two different linear extrapolations, each based on the target peak amplitude obtained with a different calibration ball diameter.

The validity of this normalization is based on the assumption of a linear relationship between object size (i.e., its cross-sectional area that is masking a portion of the infrared light beam) and its resulting Target Peak Amplitude. However, due to the non-uniform cross-sectional intensity of an infrared beam, which is greatest in the center and weakens towards its edges (FIG. 13), the empirical relationship between cross-sectional area and Target Peak Amplitude is not exactly linear but curves downward (FIG. 14). This is because, as the cross-sectional area of an object increases, the additional cross-sectional area of the beam that is masked is of lower intensity. The non-linear relationship can be approximated by a linear extrapolation derived from two points, the origin and that obtained with the calibration Basic object. Therefore, the size of the selected calibration Basic object determines the slope of the resulting linear extrapolation and therefore its accuracy in approximating the actual relationship across the range of insect sizes encountered during normal field operation. The optimal calibration Basic object cross-sectional area was empirically found to be that obtained with about a 2.5 mm diameter ball.

Although the mathematical normalization calculation could be accomplished by microcontroller 36 prior to transmission of Target Peak Amplitude data, it is left to central location device 42 in order to reduce the overhead (computational load) of microcontroller 36.

The second initialization procedure involves the system self-test feature. The microcontroller can generate a digital test pulse that results in a momentarily change in the transducer 14 output which simulates the passing of an insect near the transducer 14. By performing this self-test at regular intervals, the system can validate proper operation of each probe. For example, with a single beam or two orthogonal, intersecting beams in a horizontal plane, microcontroller 36 can generate a digital pulse (FIGS. 6 and 16, PIN 24 of PIC16F872 or PIC16F873) that results in a reduction in normal current supplied to an infrared LED(s) 30. This results in a momentary decrease in the amount of infrared light received by phototransistor 32 which simulates an insect passing through the beam. The value of the self-test current perturbation was selected to generate a similar pulse amplitude as that produced by the Basic object calibration. The self-test initialization procedure is performed on each newly manufactured probe and the resulting peak amplitude (Initial Self-test Peak Amplitude, ISPA) is permanently recorded in the microcontroller's non-volatile memory. When a probe is put into service, this Initial Self-test Peak Amplitude number is also transmitted to the central location device 42. While the probe is in service, its self-test is performed at regular intervals, for example, about every hour. The resulting peak amplitude, called the Current Self-test Peak Amplitude (CSPA) is also transmitted to the central location device 42. This Current Self-test Peak Amplitude may differ from the Initial Self-test Peak Amplitude due to changes such as component aging, environmental changes, and potential foreign matter accumulation such as dust, moisture, etc., on the transducer 14 components. In order to reduce the effect of such changes in the interpretation of the peak amplitude data, the ratio of the Initial Self-test Peak Amplitude to the Current Self-test Peak Amplitude is used as a factor to adjust the target data. Therefore, utilizing all the above calibration data, the Adjusted Target Peak Amplitude (ATPA) can be expressed as:

$$ATPA=(TPA/MBPA) \times (ISPA/CSPA)$$

This adjustment tends to make all probes appear to have identical sensitivity response performance even while they are in service for long periods under varying environmental conditions. As before, although this calculation could be accomplished by microcontroller 36, it is left to central location device 42 in order to reduce the overhead of microcontroller 36. In the case of two transducers 14 producing two beams, central location device 42 uses the two ATPAs associated with each individual falling object to calculate the Amplitude Vector Sum (AVS) for the falling object. If the actual sensitivity response degrades too much resulting in very low Target Peak Amplitudes, the probe may become unreliable or nonfunctional and require maintenance such as cleaning and/or repair. However, by continuously monitoring changes in the Current Self-test Peak Amplitude, any gradual degradation in the sensitivity response will be observed. This will allow maintenance to be scheduled and performed before catastrophic failure occurs.

Lastly, a sensor 20 software includes a data transmission sub-component of the microcontroller program which performs the task of transmitting the stored extracted parameter data, and the calibration factors back to the central location device 42 upon its request. As previously stored extracted parameter data are transmitted back, the microcontroller 36 memory is cleared for storing newly data.

The foregoing detailed description is for the purpose of illustration. Such detail is solely for that purpose and those skilled in the art can make variations without departing from the spirit and scope of the invention.

Index of the Elements
10. Microcontroller-based insect monitoring system
12. Probe
13. Upper Body Section
14. Transducer
16. Aperture
17. Funnel
20. Sensor
24. Sensor Head
25. Transducer Cable
30. Infrared Light-Emitting Diode
31. Beam
32. Phototransistor
33. Temperature Sensor
34. Probe Circuit Board
35. Beam Current Generator
36. Programmable Microcontroller
37. Internal Non-Volatile Memory
38. Current to Voltage Convertor
39. Capacitive Coupling
40. Voltage Threshold Detector
41. Bias Reference Voltage
42. Central Location Device
44. Analog Input
46. Digital Input
47. Single Interrupt Generating Digital Input
48. Digital Output
50. Multiplexer
52. Transmission Medium
54. OR Gate

What is claimed is:

1. A system for quantitative and/or qualitative detection of insect infestation in stared products comprising:
    (a) at least one probe detector containing a sensor head having at least two transducers for detecting the passage of at least one insect through said probe head and producing an analog output wherein said output is a waveform,
    (b) a circuit board operatively connected to said transducer for collecting and storing data generated by said transducer, and
    (c) a central location device operatively connected to said circuit board for collecting circuit hoard data for processing and storage.

2. The system of claim 1 wherein said sensor head has infrared transducers producing multiple beams wherein orientation and position of each beam improves the probability of capturing the largest cross-sectional area of said insect.

3. The system of claim 1 wherein said circuit board comprises a programmable microcontroller, and at least one voltage threshold detector.

4. The system of claim 3 wherein said microcontroller includes an analog input, at least one digital input, a digital output and an internal non-volatile memory.

5. The system of claim 3 wherein said microcontroller contains a computer readable medium having a software program which includes a signal processing sub-component, a calibration sub-component, and a data transmission sub-component.

6. The system of claim 5 wherein said signal processing subcomponent analyzes an incoming sensor signal to determine if the signal is produced by an insect falling through the sensor head by checking a signal present digital pulse duration; when said signal is produced by a falling insect, said sub-component determines at least one maximum analog value during a pulse interval, said sub-component time stamps said at least one determined maximum analog value, and stores said at least one value and the time stamp.

7. The system of claim 5 wherein said calibration sub-component comprises at least two response sensitivity initialization routines in order to obtain calibration factors.

8. The system of claim 1 wherein said probe includes a temperature sensor operatively connected to said circuit board.

9. A method for detecting insect infestation in stored products comprising:
   (a) placing a grain probe detector containing (1) a sensor head having at least two transducers for detecting the passage of at least one insect through the probe sensor head, and (2) a circuit board operatively connected to said transducers; into a stored product.
   (b) detecting the passage of at least one insect through the probe and providing at least one analog output, and generating a signal present digital pulse in maid circuit board based on said analog outputs,
   (c) determining if said signal is greater than threshold level,
   (d) sending said signal greater than threshold level to a microcontroller on said circuit board,
   (e) processing said signal to extract data iron said signal, and
   (f) storing said extracted data in a memory of said microcontroller.

10. A method for detecting insect infestation in stored products comprising:
    (a) placing a probe detector having (1) a sensor head having infrared transducers producing multiple beams to detecting passage of at least one insect through the probe sensor head, and (2) a circuit board operatively connected to said transducers; into a stored product,
    (b) detecting passage of at least one insect through the probe and providing at leant two analog outputs,
    (c) determining if at least one of said output are greater than threshold level,
    (d) generating at least one signal present digital pulse,
    (e) analyzing maid analog outputs to determine at least one maximum analog value,
    (f) combining individual signal present digital pulses to form a composite signal present digital pulse,
    (g) measuring the time between contiguous signal present digital pulses,
    (h) measuring a composite signal digital pulse duration, and
    (i) transmitting said maximum analog values with time stamps, time between contiguous signal present digital pulses end signal present digital pulse duration to a central location device.

11. The method of claim 10 further including calculating a vector sum of maximum analog values to obtain an insect size value.

12. The method of claim 10 further including using a mathematical classification analysis to determine insect species using the data transmitted to said central location device.

13. The method of claim 9 further comprising: p1 sending said data stored by said memory to a central location device.

14. The method of claim 13 further including calculating a vector sum of maximum analog values to obtain an insect size value.

15. The method of claim 13 further comprising using a mathematical classification analysis to determine insect species using the data transmitted to said central location device.

16. A computer readable medium encode with a software program for monitoring insects in stored products wherein said program;
    (a) analyses at least one incoming analog sensor signal when at least one incoming signal present digital pulse is detected,
    (b) measures duration of the at least one signal present digital pulse,
    (c) monitors the at least one analog sensor signal for a maximum analog value,
    (d) records and stores an at least one maximum analog value for transmission to a central location devices, and
    (e) records and stores time of occurrence of said at least one maximum analog value.

17. The computer readable medium of claim 16 wherein said program further calibrates new grain probe detectors for consistent performance by
    (a) determining a standard mean target peak amplitude creating a first calibration factor, and
    (b) recording and storing said standard mean target peak amplitude for transmission to said central location device.

18. The computer readable medium of claim 16 where said program further self-tests new grain probe detectors to validate the operation of at least one grain probe detector by
    (a) generating a digital test pulse to simulate an insect passing said transducer to obtain an initial self-test peak amplitude creating a second calibration factor,
    (b) recording and storing said initial self-test peak amplitude for transmission to a central location device.

19. The computer readable medium of claim 16 wherein said program self-tests grain probe detectors that are in operation in a stored product by;
    (a) generation a digital test pulse to simulate an insect passing said transducer to obtain a current self-test peak amplitude creating a third calibration factor,
    (b) recording and storing said current self-test peak amplitude for transmission to a central location device.

20. A method for detecting insect infestation in stored products comprising:
    (a) placing a grain probe detector containing (1) a sensor head having at least two infrared transducers for detecting passage of at least one insect through the probe sensor head, and (2) a circuit board operatively connected to said at least two transducers into a stored product,
    (b) detecting the passage of at least one insect through the probe and providing at least one analog output, and generating at least one signal present digital pulse in said circuit board based on said analog output,
    (c) determining if said at least one signal greater than threshold level,
    (d) sending amid at least one signal greater than threshold level to a microcontroller on said circuit board,
    (e) processing said signal to extract data from said at least one signal, using a computer readable medium having a software program which (1) analyzes said analog sensor signal when an incoming signal present digital pulse is detected, (2) measures duration of the signal present digital pulse, (3) records mud stores the duration of the signal present digital pulse, (4) monitors the analog sensor signal for a maximum analog value, (5) records and stores time of occurrence of said maximum analog value, (6) record and stores a maximum analog value for transmission to a central location device, (7) measures the duration of the interval between contiguous signal present digital pulses, and (8) records and stores said duration.

21. The method of claim 20 further comprising:

sending said stored data to a central location device for analysis.

22. The method of claim 21 further comprising self-testing said grain probe detectors wherein said program (1) generates a digital test pulse to simulate an insect passing said transducers to obtain a current self-test peak amplitude creating a calibration factor, (2) recording and storing said current self-test peak amplitude for transmission to a central location device.

23. The system of claim 5 wherein said signal processing subcomponent determines parameters of signal including:

(a) generating a signal present digital pulse whenever a sensor signal amplitude is greater than a threshold level, (b) analyzing at least one incoming analog sensor signal when a signal amplitudes is greater than threshold level to determine and store its maximum analog value, (c) determining duration of a signal by monitoring said signal by monitoring said signal present digital pulse, (d) determining duration of time between signals by monitoring at least two signal present digital pulses, and (e) recording a time of said signal present digital pulse and at least one determined maximum analog value, wherein said parameters are stored in a memory.

24. The system of claim 23 wherein said stored parameters are transmitted to a central location device for decision making analysis.

25. The system of claim 23 wherein said decision making analysis includes:

(a) flagging false positive events when said duration of the signal present digital pulse is outside a given range, and (b) flagging any signal present digital pulse generated within a specified retrigger interval of the previously generated signal present digital pulse.

26. The system of claim 25 wherein said range of said duration is less than about 2 millisecond or greater than about 30 milliseconds and the specified retrigger interval is about 100 milliseconds.

* * * * *